(12) United States Patent
Stoddart et al.

(10) Patent No.: US 9,085,460 B2
(45) Date of Patent: Jul. 21, 2015

(54) NANOPOROUS CARBOHYDRATE FRAMEWORKS AND THE SEQUESTRATION AND DETECTION OF MOLECULES USING THE SAME

(75) Inventors: J. Fraser Stoddart, Evanston, IL (US); Ross S. Forgan, Evanston, IL (US); Ronald A. Smaldone, Chicago, IL (US); Jeremiah J. Gassensmith, Wilmette, IL (US)

(73) Assignee: Northwestern University, Evanston, IL (US)

( * ) Notice: Subject to any disclaimer, the term of this patent is extended or adjusted under 35 U.S.C. 154(b) by 766 days.

(21) Appl. No.: 13/050,709

(22) Filed: Mar. 17, 2011

(65) Prior Publication Data

US 2012/0070904 A1    Mar. 22, 2012

Related U.S. Application Data

(60) Provisional application No. 61/314,889, filed on Mar. 17, 2010, provisional application No. 61/351,704, filed on Jun. 4, 2010.

(51) Int. Cl.
| | |
|---|---|
| C08B 37/16 | (2006.01) |
| A61K 31/724 | (2006.01) |
| A61K 31/715 | (2006.01) |
| B82Y 30/00 | (2011.01) |
| B01J 20/22 | (2006.01) |
| B01J 20/28 | (2006.01) |
| C01B 3/00 | (2006.01) |
| G01N 21/80 | (2006.01) |

(52) U.S. Cl.
CPC .............. *B82Y 30/00* (2013.01); *B01J 20/226* (2013.01); *B01J 20/2808* (2013.01); *C01B 3/0015* (2013.01); *C08B 37/0012* (2013.01); *C08B 37/0015* (2013.01); *G01N 21/80* (2013.01); *Y02C 10/08* (2013.01); *Y02E 60/328* (2013.01); *Y10T 436/204998* (2015.01)

(58) Field of Classification Search
USPC ........................................... 536/103; 514/58
See application file for complete search history.

(56) References Cited

U.S. PATENT DOCUMENTS

2006/0252641 A1    11/2006 Yaghi et al.

OTHER PUBLICATIONS

Geibelmann et al. (Angew. Chem. Int. Ed. 2005, 44, 924-927).*
Kano et al. (Journal of the American Chemical Society, Oct. 31, 2001) vol. 123, No. 43, pp. 10616-10627).*
Muzikar et al. (Electrophoresis (2002), 23(12), 1796-1802).*
Seiyama et al. (Journal of Inclusion Phenomena (1984), 2(3-4), 765-73).*
Kamitori et al. (J. Am. Chem. Soc. 1987, 109, 2409-2014).*
Klufers et al. (Angew. Chem. Int. Ed. Engl. 1994. 33. No. 18, 1863-1865).*
Kim, J. et al., "Carbohydrate Wheels: Cucurbituril-Based Carbohydrate Clusters", Angew. Chem. Int. Ed. 2007, 46, 7393-7395.
Kitagawa, S. et al., "Functional Porous Coordination Polymers", Angew. Chem. Int. Ed. 2004, 43, 2334-2375.
Klüfers, P. et al., "Homoleptic Cuprates(II) with Multiply Deprotonated α-Cyclodextrin Ligands", Chem. Eur. J. 1997, 3, 601-608.
Koltover, I., "Biomolecular Self-Assembly Stacks of viruses", Nat. Mater. 2004, 3, 584-586.
Kubota, Y. et al., "Direct Observation of Hydrogen Molecules Adsorbed onto a Microporous Coordination Polymer", Angew. Chem. Int. Ed. 2005, 44, 920-923.
Lee, J. Y. et al., "Metal-organic framework materials as catalysts", Chem. Soc. Rev. 2009, 38, 1450-1459.
Li, H. et al., "Design and synthesis of an exceptionally stable and highly porous metal-organic framework", Nature 1999, 402, 276-279.
Li, J. R., et al., "Selective gas adsorption and separation in metal-organic frameworks", Chem. Soc. Rev. 2009, 38, 1477-1504.
Li, Q. et al., "Docking in Metal-Organic Frameworks", Science Aug. 14, 2009 Issue.
Lindner, K. et al., "Crystal Structure of the γ-Cyclodextrin n-Proponal Inclusion Complex; Correlation of α-, β-, γ-Cyclodextrin Geometries", Biochem. Biophys. Res. Commun. 1980, 92, 933-938.
Livage, C. et al., "A Three-Dimensional Metal-Organic Framework with an Unprecedented Octahedral Building Unit", Angew. Chem. Int. Ed. 2005, 44, 6488-6491.
Llewellyn, P. L. et al., "Hydrogen Storage in the Giant-Pore Metal-Organic Frameworks MIL-100 and MIL-101", Angew. Chem. Int. Ed. 2006, 45, 8227-8231.
Loiseau, T. et al., "MIL-96, a Porous Aluminum Trimesate 3D Structure Constructed from a Hexagonal Network of 18-Membered Rings and u3-Oxo-Centered Trinuclear Units", J. Am. Chem. Soc. 2006, 128, 10223-10230.
Ma, L. Q. et al., "Enantioselective catalysis with homochiral metal-organic frameworks", Chem. Soc. Rev. 2009, 38, 1248-1256.
MacGillivray, L. R. et al., "Supramolecular Control of Reactivity in the Solid State: From Templates to Ladderanes to Metal-Organic Frameworks", Acc. Chem. Res. 2008, 41, 280-291.
MacGillivray, L. R. et al., "A chiral spherical molecular assembly held together by 60 hydrogen bonds", Nature 1997, 389, 469-472.
MacGillivray, L. R., "Organic Synthesis in the Solid State via Hydrogen-Bond-Driven Self-Assembly", J. Org. Chem. 2008, 73, 3311-3317.
Matsuda, R. et al., "Highly controlled acetylene accommodation in a metal-organic microporous material", Nature 2005, 436, 238-241.
Millward, A. R. et al., "Metal-Organic Frameworks with Exceptionally High Capacity for Storage of Carbon Dioxide at Room Temperature", J. Am. Chem. Soc. 2005, 127, 17998-17999.
Mulfort, K. L. et al., "Alkali Metal Cation Effects on Hydrogen Uptake and Binding in Metal-Organic Frameworks", Inorg. Chem. 2008, 47, 7936-7938.
Mulfort, K. L. et al., "Chemical Reduction of Metal-Organic Framework Materials as a Method to Enhance Gas Uptake and Binding", J. Am. Chem. Soc. 2007, 129, 9604-9605.
Nepogodiev, S. A. et al., "Synthetic Cyclic Oligosaccharides", Chem. Rev. 1998, 98, 1919-1958.

(Continued)

*Primary Examiner* — Shaojia Anna Jiang
*Assistant Examiner* — Michael C Henry
(74) *Attorney, Agent, or Firm* — Reinhart Boerner Van Deuren s.c.

(57) ABSTRACT

Disclosed are cyclodextrin-based metal organic frameworks comprising a metal cation and cyclodextrin or a cyclodextrin derivative. These metal organic frameworks are permanently porous and capable of molecule storage.

18 Claims, 19 Drawing Sheets

(56) References Cited

OTHER PUBLICATIONS

Nepogodiev, S. A. et al., "Cyclodextrin-Based Catenanes and Rotaxanes", Chem. Rev. 1998, 98, 1959-1976.

Rao, K. et al., "Stereoselective Photodimerization of (E)-Stilbenes in Crystalline y-Cyclodextrin Inclusion Complexes", J. Org. Chem. 1999, 64, 8098-8104.

Rosi, N. L. et al., "Hydrogen Storage in Microporous Metal-Organic Frameworks", Science 2003, 300, 1127-1129.

Rowsell, J. L. C. et al., "Metal-organic frameworks: a new class of porous materials", Microporous Mesoporous Mater. 2004, 73, 3-14.

Rowsell, J.L. C. et al., "Strategies for Hydrogen Storage in Metal-Organic Frameworks", Angew. Chem. Int. Ed. 2005, 44, 4670-4679.

Rowsell, J.L. C. et al., "Gas Adsorption Sites in a Large-Pore Metal-Organic Framework", Science 2005, 309, 1350-1354.

Sanchez, C. et al., "Applications of hybrid organic-inorganic nanocomposites", J. Mater. Chem. 2005, 15, 3559-3592.

Stefano, L. et al., "Guanosine Hydrogen-Bonded Scaffolds: A New Way to Control the Bottom-Up Realisation of Well-Defined Nanoarchitectures", Chem. Eur. J. 2009, 15, 7792-7806.

Stoddart, J. F. et al., "Big and little Meccano", Tetrahedron 2008, 64, 8231-8263.

Stoddart, J. F., "The chemistry of the mechanical bond", Chem. Soc. Rev. 2009, 38, 1802-1820.

Sudik, A. C. et al., "Design, Synthesis, Structure, and Gas ($N_2$, Ar, $CO_2$, $CH_4$, and $H_2$) Sorption Properties of Porous Metal-Organic Tetrahedral and Heterocuboidal Polyhedra", J. Am. Chem. Soc. 2005, 127, 7110-7118.

Sue, C, et al., "Enabling tetracationic cyclophane production by trading templates", Chem. Sci., 2010, 1, 119-125.

Tanabe, K. K. et al., "Systematic Functionalization of a Metal-Organic Framework via a Postsynthetic Modification Approach", J. Am. Chem. Soc. 2008, 130, 8508-8517.

Thallapally, P. K. et al., "Flexible (Breathing) Interpenetrated Metal-Organic Frameworks for $CO_2$ Separation Applications", J. Am. Chem. Soc. 2008, 130, 16842-16843.

Ulijn, R. V. et al., "Designing peptide based nanomaterials", Chem. Soc, Rev. 2008, 37, 664-675.

Vaidhyanathan, R. et al., "An amine-functionalized metal organic framework for preferential $CO_2$ adsorption at low pressuress", Chem. Commun. 2009, 5230-5232.

Vriezema, D. M. et al., "Self-Assembled Nanoreactors", Chem. Rev. 2005, 105, 1445-1489.

Walton, K. S. et al., "Understanding Inflections and Steps in Carbon Dioxide Adsorption Isotherms in Metal-Organic Frameworks", J. Am. Chem. Soc. 2008, 130, 406-407.

Wang, Q. et al., "Natural Supramolecular Building Blocks: Cysteine-Added Mutants of Cowpea Mosaic Virus", Chemistry & Biology 2002, 9, 813-819.

Wang, X. et al., "Application of Nanotechnology in Cancer Therapy and Imaging", CA—Cancer J. Clin. 2008, 58, 97-110.

Wang, Z. et al., "Postsynthetic modification of metal-organic frameworks", Chem. Soc. Rev. 2009, 38, 1315-1329.

Whitesides, G. M. et al., "Self-Assembly at All Scales", Science 2002, 295, 2418-2421.

Wong-Foy, A. G. et al., "Exceptional $H_2$ Saturation Uptake in Microporous Metal-Organic Frameworks", J. Am. Chem. Soc. 2006, 128, 3494-3495.

Yaghi, O. M. et al., "Hydrothermal Synthesis of a Metal-Organic Framework Containing Large Rectangular Channels", J. Am. Chem. Soc. 1995, 117, 10401-10402.

Yaghi, O. M. et al., "Selective binding and removal of guests in a microporous metal-organic framework", Nature 1995, 378, 703-706.

Yaghi, O. M. et al., "Reticular synthesis and the design of new materials", Nature 2003, 423, 705-714.

Yeager, M. et al., "Supramolecular organization of immature and mature murine leukemia virus revealed by electron cryo-microscopy: Implications for retroviral assembly mechanisms", A. Proc. Nat. Acad. Sci. 1998, 95, 7299-7304.

Zhao, Z.; Li, Z.; Lin, Y. S.; "Adsorption and Diffusion of Carbon Dioxide on Metal-Organic Framework (MOF-5)", Ind. Eng. Chem. Res. 2009, 48, 10015-10020.

Geibelmann, A., et al., Carbohydrate-metal interactions shaped by supramolecular assembling. Angewan dte Chemie International Edition, Jan. 28, 2005, vol. 44, pp. 924-927.

Smaldon, R.A., et al., Metal-organic frameworks from edible natural products. Angewandte Chemie International Edition, Nov. 8, 2010, vol. 49, pp. 8630-8634.

International Search Report from PCT/US2011/028866 issued Dec. 15, 2011.

Amirsakis, D. G. et al., "Host-Guest Chemistry Aids and Abets a Stereospecific Photodimerization in the Solid State", Angew. Chem. Int. Ed. 2001, 40, 4256-4261.

Amirsakis, D. G. et al., "Diastereospecific Photochemical Dimerization of a Stillbene-Containing Daisy Chain Monomer in Solution as well as in the Solid State", Angew. Chem. Int. Ed. 2003, 42, 1126-1132.

An, J. et al., "Cation-Triggered Drug Release from a Porous Zinc-Adeninate Metal-Organic Framework", J. Am. Chem. Soc. 2009, 131, 8376-8377.

An, J. et al., "Synthesis, Structure, Assembly, and Modulation of the $CO_2$ Adsorption Properties of a Zinc-Adeninate Macrocycle", J. Am. Chem. Soc. 2009, 131, 8401-8403.

Angelescu, D. G. et al., "Viruses as supramolecular self-assemblies: modelling of capsid formation and genome packaging", Soft Matter 2008, 4, 1981-1990.

Arstad, B.; Fjellvag, H.; Kongshaug, K. O.; Swang, O.; Blom, R., "Amine functionalised metal organic frameworks (MOFs) as adsorbents for carbon dioxide", Adsorption 2008, 14, 755-762.

Ban, Y. S.; Farha, O. K.; Hupp, J. T.; Snurr, R. Q., "Enhancement of $CO_2/N_2$ selectivity in a metal-organic framework by cavity modification", J. Mater. Chem. 2009, 19, 2131-2134.

Banerjee, R. et al., "Control of Pore Size and Functionality in Isoreticular Zeolitic Imidazolate Frameworks and their Carbon Dioxide Selective Capture Properties", J. Am. Chem. Soc. 2009, 131, 3875-3877.

Banerjee, R. et al., "High-Throughput Synthesis of Zeolitic Imidazolate Frameworks and Application to $CO_2$ Capture", Science 2008, 319, 939-943.

Bath, J. et al., "DNA nanomachines", Nat. Nanotechnol. 2007, 2, 275-284.

Benner, K. et al., "Cyclodextrin Bucket Wheels: An Oligosaccharide Assembly Accommodates Metal(IV) Centers", Angew. chem. Int. Ed. 2006, 45, 5818-5822.

Blomquist, A. et al., "Li-decorated metal-organic framework 5: A route to achieving a suitable hydrogen storage medium", Proc. Natl. Acad. Sci. U.S.A. 2007, 104, 20173-20176.

Boger, J. et al., "Symmetrical Triamino-per-O-methyl-α-cyclodextrin: Preparation and Characterization of Primary Trisubstituted α-Cyclodextrins", J. Am. Chem. Soc. 1979, 7630-7631.

Bonacchi, D. et al., "Nanosized Iron Oxide Particles Entrapped in Pseudo-Single Crystals γ-Cyclodextrin", Chem. Mater. 2004, 16, 2016-2020.

Britt, D. et al., "Metal-organic frameworks with high capacity and selectivity for harmful gases", Proc. Nat. Acad. Sci. 2008, 105, 11623-11627.

Britt, D.; Furukawa, H.; Wang, B.; Glover, T. G.; Yaghi, O. M.; "Highly efficient separation of carbon dioxide by a metal-organic framework replete with open metal sites", Proc. Nat. Ac. Sci. 2009, 106, 20637-2064.

Burrows, A. D. et al., "Sulfur-tagged metal-organic frameworks and their post-synthetic oxidation", Chem. Commun. 2009, 4218-4220.

Caskey, S. R. et al., "Dramatic Tuning of Carbon Dioxide Uptake via Metal Substitution in a Coordination Polymer with Cylindrical Pores", J. Am. Chem. Soc. 2008, 130, 10870-10871.

Chen, B. et al., "High $H_2$ Adsorption in a Microporous Metal-Organic Framework with Open Metal Sites", Angew. Chem. Int. Ed. 2005, 44, 4745-4749.

Chen, S. M. et al., "Spontaneous Resolution of Racemic Camphorates in the Formation of Three-Dimensional Metal Organic Frameworks", Inorg. Chem. 2009, 48, 6356-6358.

(56) References Cited

OTHER PUBLICATIONS

Chen, S. M.; Zhang, J. et al., "Multiroute Synthesis of Porous Anionic Frameworks and Size-Tunable Extraframework Organic Cation-Controlled Gas Sorption Properties", J. Am. Chem. Soc. 2009, 131, 16027-16029.

Conn, M. et al., "Self-Assembling Capsules", Chem. Rev. 1997, 97, 1647-1668.

Cote, A. P. et al., "Porous, Crystalline, Covalent Organic Frameworks", Science 2005, 310, 1166-1170.

Dankers, P. Y. W. et al., "Supramolecular Biomaterials. A Modular Approach towards Tissue Engineering", Bull. Chem. Soc. Jpn. 2007, 80, 2047-2073.

Demessence, A.; D'Alessandro, D. M.; Foo, M. L.; Long, J. R., "Strong $CO_2$ Binding in a Water-Stable, Triazolate-Bridged Metal-Organic Framework Functionalized with Ethylenediamine", J. Am. Cheat. Soc. 2009, 131, 8784-8786.

Dinca, M. et al., "Hydrogen Storage in Microporous Metal-Organic Frameworks with Exposed Metal Sites", Angew. Chem. Int. Ed. 2008, 47, 6766-6779.

Eddaoudi, M. et al., "Modular Chemistry: Secondary Building Units as a Basis for the Design of Highly Porous and Robust Metal-Organic Carboxylate Frameworks", Acc. Chem. Res. 2001, 34, 319-330.

Eddaoudi, M. et al., "Systematic Design of Pore Size and Functionality in Isoreticular MOFs and Their Application in Methane Storage", Science 2002, 295, 469-472.

El-Kaderi, H. M. et al., "Designed Synthesis of 3D Covalent Organic Frameworks", Science 2007, 316, 268-272.

Endo, M. et al., "Porphyrin Light-Harvesting Arrays Constructed in the Recombinant Tobacco Mosaic Virus Scaffold", Chem. Eur. J. 2007, 13, 8660-8666.

Farha, O. K. et al., "Synthesis and Hydrogen Sorption Properties of Carborane Based Metal-Organic Framework Materials", J. Am. Chem. Soc. 2007, 129, 12680-12681.

Férey, G., "Hybrid porous solids: past, present, future", Chem. Soc. Rev, 2008, 37, 191-214.

Fuchs, R. et al., "Multinuclear Sandwich-type Complexes of Deprotonated β-Cyclodextrin and Copper(II) Ions", Angew. Chem. Int. Ed. Engl. 1993, 32, 852-854.

Férey, G. et al., "Mixed-Valence Li/Fe-Based Metal-Organic Frameworks with Both Reversible Redox and Sorption Properties", Angew. Chem. Int. Ed. 2007, 46, 3259-3263.

Gadzikwa, T. et al., "A Zn-based, pillared paddlewheel MOF containing free carboxylic acids via covalent post-synthesis elaboration", Chem. Commun. 2009, 3720-3722.

Garcia-Garibay, M. A.,"Engineering Carbene Rearrangements in Crystals: From Molecular Information to Solid-State Reactivity", Acc. Chem. Res. 2003, 36, 491-498.

Geisselmann, A. et al.,"Carbohydrate-Metal Interactions Shaped by Supramolecular Assembling", Angew. Chem. Int. Ed. 2005, 44, 924-927.

Griffiths, K. E. et al., "Template-directed synthesis of donor/acceptor [2]catenanes and [2]rotaxanes", Pure Appl. Chem. 2008, 80, 485-506.

Han, S. S. et al., "Improved Designs of Metal-Organic Frameworks for Hydrogen Storage", Angew. Chem. Int. Ed. 2007, 46, 6289-6292.

Han, S. S. et al., "Lithium-Doped Metal-Organic Frameworks for Reversible H2 Storage at Ambient Temperature", J. Am. Chem. Soc. 2007, 129, 8422-8423.

Harata, K., "The Structure of the Cyclodextrin Complex. XX. Crystal Structure of Uncomplexed Hydrated y-Cyclodextrin", Bull. Chem. Soc. Jpn. 1987, 60, 2763-2767.

Harata, K., "Crystal Structure of y-Cyclodextrin at Room Temperature", Chem. Lett. 1984, 641-644.

Herrmann, W. et al., "Supramolecular control of the photochemistry of stilbenes by cyclodextrins", Chem. Commun. 1997, 1709-1710.

Horcajada, P. et al., "Metal-Organic Frameworks as Efficient Materials for Drug Delivery", Angew. Chem. Int. Ed. 2006, 45, 5974-5978.

Horcajada, P. et al., "Flexible Porous Metal-Organic Frameworks for a Controlled Drug Delivery", J. Am. Chem. Soc. 2008, 130, 6774-6780.

Jones, J. K. N. et al., "Large heterocyclic rings from carbohydrate precursors", Can. J. Chem. 1969, 47, 3213-3215.

Kamitori, S. et al., "Crystal and Molecular Structure of Double Macrocyclic Inclusion Complexes, y-Cyclodextrin • 12-Crown-4 • NaCl, a Model for the Transport of Ions through Membranes", Bull. Chem. Soc. Jpn. 1988, 61, 3825-3830.

Kay, E. R. et al., "Synthetic Molecular Motors and Mechanical Machines", Angew. Chem. Int. Ed. 2007, 46, 72-191.

Kaye, S. S. et al., "Impact of Preparation and Handling on the Hydrogen Storage Properties of Zn4O(1,4-benzenedicarboxylate)3 (MOF-5)", J. Am. Chem. Soc. 2007, 129, 14176-14177.

Khashab, N. M. et al., "Redox- and pH-Controlled Mechanized Nanoparticles", Eur. J. Org. Chem. 2009, 1669-1673.

\* cited by examiner

NANOPOROUS CARBOHYDRATE FRAMEWORKS AND THE SEQUESTRATION AND DETECTION OF MOLECULES USING THE SAME

This application claims priority from U.S. Provisional Patent Application Ser. Nos. 61/314,889 filed on Mar. 17, 2010 and 61/351,704 filed on Jun. 4, 2010, each of which are incorporated herein by reference in its entirety.

This invention was made with government support under Grant No. CHE-0924620 awarded by the National Science Foundation. The government has certain rights in the invention.

FIELD OF THE INVENTION

The present invention relates generally to environmental friendly metal organic frameworks assembled in water from renewable and biodegradable ingredients under ambient conditions. These metal organic frameworks are permanently porous and capable of small molecule storage. Specifically, the invention relates to metal organic frameworks comprising alkali metal salts and γ-cyclodextrin (γCD), a cyclic carbohydrate that is non-toxic and can be mass produced enzymatically from renewable feedstocks; and applications thereof.

BACKGROUND OF THE INVENTION

When chemists respond creatively to the abstract world of design, and then execute their designs through a practice, which has become known as synthesis, then chemistry becomes an extremely powerful artistic medium in which to forge new materials with potentially awesome functions. Over more than a couple of centuries now, chemists have come to appreciate the role of atoms that constitute the different elements to not only form molecules, but also to make molecules. While nature bears adequate witness to the former, the chemist is the maker of molecules with no holds barred. Thus, chemists have explored the interactions between the atoms and molecules at the covalent, coordinative (dative) and noncovalent levels of bonding. During the past half century, a growing appreciation of the importance of the noncovalent bond has propelled chemistry beyond the molecule to what Jean-Marie Lehn (Lehn, J. M., *Supramolecular Chemistry: Concepts and Perspectives*, Wiley-VCH, 1995, 271 pp) refers to as supramolecular chemistry. In more recent times, the concepts of molecular recognition and self-assembly (Whitesides, G. M. et al., *Science* 2002, 295, 2418-2421) have been employed in syntheses that are template-directed (Griffiths, K. E. et al., *Pure Appl. Chem.* 2008, 80, 485-506) in order to create efficiently an additional chemical bond, namely the mechanical bond (Stoddart, J. F. et al., *Tetrahedron* 2008, 64, 8231-8263; Stoddart, J. F., *Chem. Soc. Rev.* 2009, 38, 1802-1820). By introducing the mechanical bond into chemistry, chemists have managed to integrate weak noncovalent with strong covalent bonding to create within molecules a unique range of intriguing properties with the potential for far-reaching applications in the rapidly expanding arena of molecular nanotechnology (Kay, E. R. et al., *Angew. Chem. Int. Ed.* 2007, 46, 72-191).

Today, there is a need for chemists to reach out beyond the molecule in another way that is every bit as robust as building mechanical bonds into molecules; it is to create extended networks of atoms by designing and constructing new crystalline solids from molecular building blocks, such that the molecule is the "crystal" and the crystal is the "molecule". Endowed potentially with many of the properties (e.g., binding, reactivity, catalysis, etc.) that small and not so small molecules enjoy, these so-called (Yaghi, O. M. et al., *J. Am. Chem. Soc.* 1995, 117, 10401-10402) metal-organic frameworks (MOFs) have given rise to a completely new field of materials science that has been christened (Yaghi, O. M. et al., "Reticular Synthesis and the Design of New Materials," *Nature* 2003, 423, 705-714) "reticular chemistry" by its leading proponent, Omar Yaghi. During the past decade, the field of reticular chemistry has developed a pace in the research laboratories, not only of Yaghi (Yaghi, O. M. et al., *Nature* 1995, 378, 703-706; Eddaoudi, M. et al., *Science* 2002, 295, 469-472; Rosi, N. L. et al., *Science* 2003, 300, 1127-1129; Chen, B. et al., *Angew. Chem. Int. Ed.* 2005, 44, 4745-4749; Sudik, A. C. et al., *J. Am. Chem. Soc.* 2005, 127, 7110-7118; Rowsell, J. et al., *Angew. Chem. Int. Ed.* 2005, 44, 4670-4679; Millward, A. R. et al., *J. Am. Chem. Soc.* 2005, 127, 17998-17999; Cote, A. P. et al., *Science* 2005, 310, 1166-1170; Rowsell, J. et al., *Science* 2005, 309, 1350-1354; Wong-Foy, A. G. et al., *J. Am. Chem. Soc.* 2006, 128, 3494-3495; Kaye, S. S. et al., *J. Am. Chem. Soc.* 2007, 129, 14176-14177; Walton, K. S. et al., *J. Am. Chem. Soc.* 2008, 130, 406-407; El-Kaderi, H. M. et al., *Science* 2007, 316, 268-272; Banerjee, R. et al., *Science* 2008, 319, 939-943), but also of Férey (Livage, C. et al., *Angew. Chem. Int. Ed.* 2005, 44, 6488-6491; Horcajada, P. et al., *Angew. Chem. Int. Ed.* 2006, 45, 5974-5978; Latroche, M.; Surblé, S.; Serre, C.; Mellot-Draznieks, C.; Llewellyn, P. L. et al., *Angew. Chem. Int. Ed.* 2006, 45, 8227-8231; Loiseau, T. et al., *J. Am. Chem. Soc.* 2006, 128, 10223-10230; Férey, G. et al., *Angew. Chem. Int. Ed.* 2007, 46, 3259-3263), Kitagawa (Matsuda, R. et al., *Nature* 2005, 436, 238-241; Kubota, Y. et al., *Angew. Chem. Int. Ed.* 2005, 44, 920-923), Hupp (Farha, O. K. et al., *J. Am. Chem. Soc.* 2007, 129, 12680-12681; Lee, J. Y. et al., *Chem. Soc. Rev.* 2009, 38, 1450-1459; Gadzikwa, T. et al., *Chem. Commun.* 2009, 3720-3722; Mulfort, K. L. et al., *Inorg. Chem.* 2008, 47, 7936-7938) and many others (Han, S. S. et al., *J. Am. Chem. Soc.* 2007, 129, 8422-8423; Han, S. S. et al., *Angew. Chem. Int. Ed.* 2007, 46, 6289-6292; Mulfort, K. L. et al., *J. Am. Chem. Soc.* 2007, 129, 9604-9605; Ma, L. Q. et al., *Chem. Soc. Rev.* 2009, 38, 1248-1256; Chen, S. M. et al., *Inorg. Chem.* 2009, 48, 6356-6358; Burrows, A. D. et al., *Chem. Commun.* 2009, 4218-4220; Blomqvist, A. et al., *Proc. Natl. Acad. Sci. U.S.A.* 2007, 104, 20173-20176; Tanabe, K. K. et al., *J. Am. Chem. Soc.* 2008, 130, 8508-8517; An, J. et al., *J. Am. Chem. Soc.* 2009, 131, 8401-8403; Dinca, M. et al., *Angew. Chem. Int. Ed.* 2008, 47, 6766-6779; Thallapally, P. K. et al., *J. Am. Chem. Soc.* 2008, 130, 16842-16843). The fundamentals of the science are taking shape very quickly and are being fueled by the enormous potential these highly porous reticular materials hold. Many, including Robert Service (Service, R. F. "Framework Materials Grab $CO_2$ and Researchers' Attention," *Science* 2008, 319, 893) at Science, believe that "MOFs and related compounds are one of the hottest playgrounds in chemistry" today.

The synthesis of complex and highly functional structures through the self-assembly of simple building blocks is commonly observed both in nature (Angelescu, D. G. et al., *Soft Matter* 2008, 4, 1981-1990; Koltover, I. *Nat. Mater.* 2004, 3, 584-586; Yeager, M. et al., *A. Proc. Nat. Acad. Sci.* 1998, 95, 7299-7304) and in the laboratory (Conn, M. et al., *Chem. Rev.* 1997, 97, 1647-1668; Kim, J. et al., *Angew. Chem. Int. Ed.* 2007, 46, 7393-73; Vriezema, D. M. et al., *Chem. Rev.* 2005, 104, 1445-1490). This "bottom-up" approach has also proved promising for the fabrication of nanoscale materials and devices (Bath, J. et al., *Nat. Nanotechol.* 2007, 2, 275-284; Ulijn, R. V. et al., *Chem. Soc. Rev.* 2008, 37, 664-675; Endo, M. et al., *Chem. Eur. J.* 2007, 13, 8660-8666; Wang, Q. et al., *Chemistry & Biology* 2002, 9, 813-819). In the last decade, this strategy has led to the discovery of MOFs (Eddaoudi, M. et al., *Acc. Chem. Res.* 2001, 34, 319-330; Li, H. et al., *Nature* 1999, 402, 276-279), which have demonstrated great promise as storage materials for gaseous small molecules in carbon capture and clean energy applications (Britt, D. et al., *Proc. Nat. Acad. Sci.* 2008, 105, 11623-11627; Rowsell, J. L. C. et al., *Angew. Chem. Int. Ed.* 2005, 44, 4670-4679). In addition, other molecules (e.g., drugs, small organic molecules) can be stored in the cavities of MOFs, opening the possibility for smart drug delivery devices or molecular sequestration (An, J. et al., *J. Am. Chem. Soc.* 2009, 131, 8376-8377; Horcajada, P. et al., *J. Am. Chem. Soc.* 2008, 130, 6774-6780; Sanchez, C. et al., *J. Mater. Chem.* 2005, 15, 3559-3592). The large void spaces in MOFs can also be utilized as a scaffold for the placement of molecular receptors yielding robust, nanoscale devices in the solid state.

In a specific example, sequestration of carbon dioxide from gaseous waste streams in the purification of petrol compounds has become a pressing issue for the scientific and global community in light of the predicted detrimental effects of anthropogenic $CO_2$ production. Recently, several approaches toward this goal have emerged using metal organic frameworks (MOFs) derived from petrochemical sources (Rowse J. L. C. et al., *Microporous Mesoporous Mater.* 2004, 73, 3; Kitagawa, S. et al., *Angew. Chem.*, Int. Ed. 2004, 43, 2334; Ferey, G. *Chem. Soc. Rev.* 2008, 37, 191; Li, J. R., et al., *Chem. Soc. Rev.* 2009, 38, 1477). Free hydroxyl and amine residues are known to react with carbon dioxide to form carbonic acids and carbamic acids respectively. These functionalities have been added to MOFs by rational design of struts (Caskey, S. R. et al., 3.1. *Am. Chem. Soc.* 2008, 130, 10870; Demessence, A. et al., *J. Am. Cheat. Soc.* 2009, 131, 8784; Ban, Y. S. et al., *J. Mater. Chem.* 2009, 19, 2131; Arstad, B. et al., *Adsorption* 2008, 14, 755; Banerjee, R. et al., *J. Am. Chesil. Soc.* 2009, 131, 3875; Vaidhyanathan, R. et al., *Chem. Commun.* 2009, 5230; Chen, S. M.; Zhang, J. et al., *J. Am. Chem. Soc.* 2009, 131, 16027; An, J. et al., *J. Ant. Chem. Soc.* 2009, 131, 8401. While these advances are noteworthy in their incremental storage capacity, they are generally synthesized from environmentally malevolent materials and solvents. Recent examples have been reported that use biological molecules, but these biomolecules do not comprise the fullness of the MOF. Further, once they have fully adsorbed the full content of their gaseous payload, they do not provide a mechanism by which to alert an end user that the material needs to be emptied or changed.

However the majority of MOF structures reported to date are composed of toxic heavy metals and struts derived from non-renewable petrochemical feedstocks and assembled in harmful organic solvents at high pressures and temperature. Therefore, the assembly of functional materials from simple components that are renewable and biocompatible is desirable in a wide variety of applications, from drug delivery devices (non-toxic) (Wang, X. et al., *CA—Cancer J. Clin.* 2008, 58, 97-110) to nanoscale device fabrication (Dankers, P. Y. W. et al., *Bull. Chem. Soc. Jpn.* 2007, 80, 2047-2073; Stefano, L. et al., *Chem. Eur. J.* 2009, 15, 7792-7806).

SUMMARY OF THE INVENTION

In light of the foregoing, it is an object of the present invention to provide cyclodextrin-based metal organic framework (CD-MOF). It is also an object of the invention to provide a method for synthesizing such CD-MOFs.

It is yet another object of the invention to provide a CD-MOF for sequestering and/or detecting molecules such as, for example, carbon dioxide, hydrogen, organophosphates, chemical warfare agents, as well as other electrophilic toxins, into the cavities and channels of CD-MOFs either during their self-assembly (crystallization) or after their formation, or both.

It is still another object of the invention to provide a CD-MOF for sequestering and/or detecting particles into the cavities and channels of CD-MOFs either during their self-assembly (crystallization) or after their formation, or both.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom.

DETAILED DESCRIPTION OF THE INVENTION

Preparation and Characterization of CD-MOFs

Figure 1:
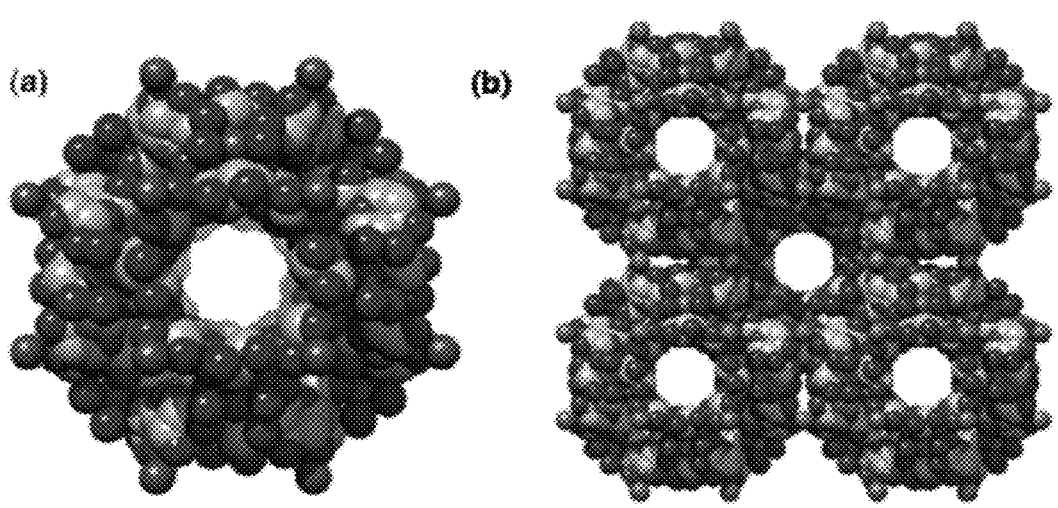
FIG. 1 depicts a space-filling representation of the orange single crystals containing azobenzene dicarboxylic acid, γCD and K$^+$ ions (CD-MOF-1). Views of (a) one nanocontainer and (b) a cluster of five nanocontainers taken from the packing diagram in the solid state.

Accordingly, the present invention includes cyclodextrin-based metal organic framework (CD-MOFs) comprising at least one metal cation and cyclodextrin or a cyclodextrin derivative. Suitable metal cations included Group I metals, Group II metals and transition metals, preferably Group I metals more preferably $Na^+$, $K^+$, $Rb^+$ or $Cs^+$. Suitable cyclodextrins are, for example, α-, β- and γ-cyclodextrins. Suitable cyclodextrin derivatives are those depicted below for Formula I.

Illustrating certain non-limiting aspects and embodiments of this invention, CD-MOFs are prepared. Cyclodextrins (Nepogodiev, S. A. et al., *Chem. Rev.* 1998, 98, 1959-1976) and their synthetic analogs (Nepogodiev, S. A. et al., *Chem. Rev.* 1998, 98, 1919-1958) have been used in a variety of procedures (Jones, J. K. N. et al., *Can. J. Chem.* 1969, 47, 3213-3215; Khashab, N. M. et al., *Eur. J. Org. Chem.* 2009, 1669-1673). Many of such cyclodextrins have been predominately alpha or beta. Previously described solid-state structures of complexed (Lindner, K. et al., *Biochem. Biophys. Res. Commun.* 1980, 92, 933-938; Kamitori, S. et al., *Bull. Chem. Soc. Jpn.* 1988, 61, 3825-3830) and uncomplexed hydrated (Harata, K., *Chem. Lett.* 1984, 641-644; Harata, K., *Bull. Chem. Soc. Jpn.* 1987, 60, 2763-2767) γCD reveal the commoner garden cage-type and channel-type packing that has prevailed in the solid-state superstructures in the case of α-CD and β-CD for decades of close investigation. It does appear, however, that the four-fold symmetry of γCD with its $C_8$ point group that has led to the formation of nanocapsules (MacGillivray, L. R. et al., *Nature* 1997, 389, 469-472) by calixarenes, thanks to self-assembly during crystallization driven largely by hydrogen bonding, has delivered a somewhat similar superstructure in the case of γ-CD, thanks to electrostatic interactions provided by appropriate metal ions. In his 1989 review on "Complexes of Metal Cations with Carbohydrates in Solution" in *Adventures in Carbohydrate Chemistry and Biochemistry*, Stephen Angyal began by noting that "complex formation between salts and carbohydrates is not a new subject," and states that crystalline adducts of sugars with inorganic salts have been studied since 1825 (Angyal, S. J., *Adv. Carb. Chem. Biochem.* 1989, 47, 1-43). In his review, Angyal points out that, substrate variation taken into consideration, metal cations can be arrayed according to their increasing tendency to form complexes with carbohydrates roughly as follows: $Li^+$, $K^+$, $Rb^+$, $Na^+$, $Mg^{2+}$, $Cd^{2+}$, $Sn^{2+}$, $Ag^+$, $Yb^+$, $Ba^{2+}$, $Sr^{2+}$, $Ca^{2+}$, $Pb^{2+}$, and $La^{3+}$. In more recent times, Geisselmann et al. (Geisselmann, A. et al., *Angew. Chem. Int. Ed.* 2003, 44, 924-927) have investigated how carbohydrate-metal interactions are shaped by "supramolecular assembly", with references to α- and β-CDs in particular (Klüfers, P. et al., *Chem. Eur. J.* 1997, 3, 601-608; Benner, K. et al., *Angew. Chem. Int. Ed.* 2006, 45, 5818-5822; Fuchs, R. et al., *Angew. Chem. Int. Ed. Engl.* 1993, 32, 852-854). They point out that both iron and manganese, at least in their higher oxidation states, are sufficiently Lewis acidic to stabilize multiply deprotonated carbohydrate ligands, forming complexes of very high stabilities and pointing out that deprotonated carbohydrate ligands are present in the active centers of carbohydrate-directed metal enzymes such as xylose isomerase. This consideration is one that has to be at least contemplated in the case of the new CD-MOFs.

Generally, CD-MOFs are prepared by dissolution of both the cyclodextrin component and the metal salt component in any solvent in which both have solubility. Isolation of CD-MOFs is done by addition of a solvent in which either of the components has poor solubility, including, but not limited to, $C_1$-$C_{18}$ alcohols, acetone, tetrahydrofuran, dioxane, acetonitrile, as well as other common organic solvents miscible with water, or any mixtures thereof. As such, in a specific non-limiting embodiment of the invention, methanol is allowed to vapor diffuse into an aqueous solution containing $K_2$abdc and γCD in a molar ratio of 2:1. Orange cubic single crystals (ca. 1 $mm^3$) are obtained and are subjected to X-ray crystallography. The crystal structure (FIG. 1) with its I432 space group is unique by comparison with all other known fully-solved, solid-state structures incorporating γCD in the literature. Moreover, the unit cell of ca. 30,000 $Å^3$ is much larger than anything that has been observed previously incorporating γCD, with one exception (Bonacchi, D. et al., *Chem. Mater.* 2004, 16, 2016-2020).

Single crystals of γ-$Fe_2O_3$/γCD are obtained by a procedure described by this reference. Ferrous chloride is added to a solution obtained by dissolving γCD in DMF and the solution is stirred under argon for two hours. An ethanolic solution of NaOH is then added and the resulting solution is stirred and exposed to air. Cubic-shaped reddish-orange single crystals separated out after a few weeks from the filtered solution under ethanol diffusion. From the full diffraction set collected at 100 K, a cubic unit cell with a 30.217 Å edge is determined. The symmetry and systematic absences of the reciprocal lattice are consistent with I432, a space group that has never been observed for γCD or any of its complexes.

Figure 11:
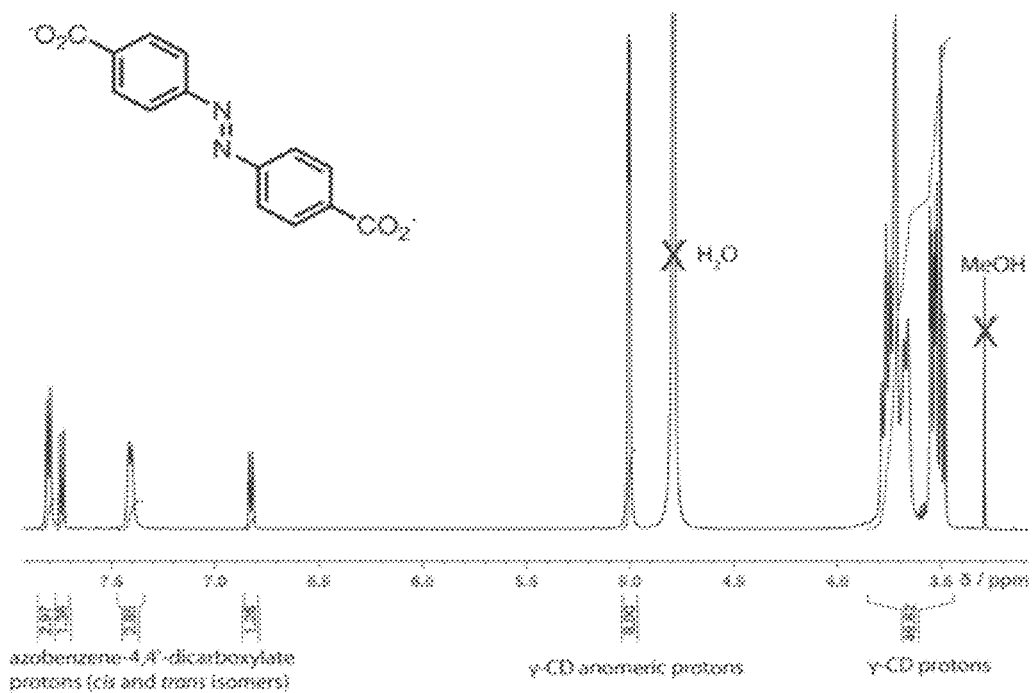
FIG. 11 is a $^1$H NMR Spectrum of CD-MOF-1 identifying the presence of counterions and thereby confirming γCD is not deprotonated.

Since it is only possible to identify clearly γCD units and $K^+$ ions in the X-ray crystal structure depicted in FIG. 1, a range of much simpler potassium salts (other than $K_2$abdc) is examined for their abilities to form crystals in aqueous methanol. Although colorless cubic crystals are obtained using both KOH and $K_2O_3$, the crystallization process is very much slower for the carbonate than for the hydroxide. This observation has led to the proposition that the $OH^-$ ions (and $CO_3^{2-}$ ions) deprotonate each γCD ring (twice) during the crystallization process. In the case of $K_2$abdc, it is presumably the conjugate base that deprotonates the γCD ring. However, $^1$H NMR Spectroscopy has identified the presence of counterions throughout the crystal lattice, thereby confirming that γCD is indeed not deprotonated (FIG. 11). These conditions involve mixing 1 equivalent of γCD with 8 equivalents of KOH or $K_2CO_3$ in water, followed by slow diffusion of methanol into the solution during 2-7 days. The crystal structure obtained using KOH is presented in FIG. 2.

Figure 2:
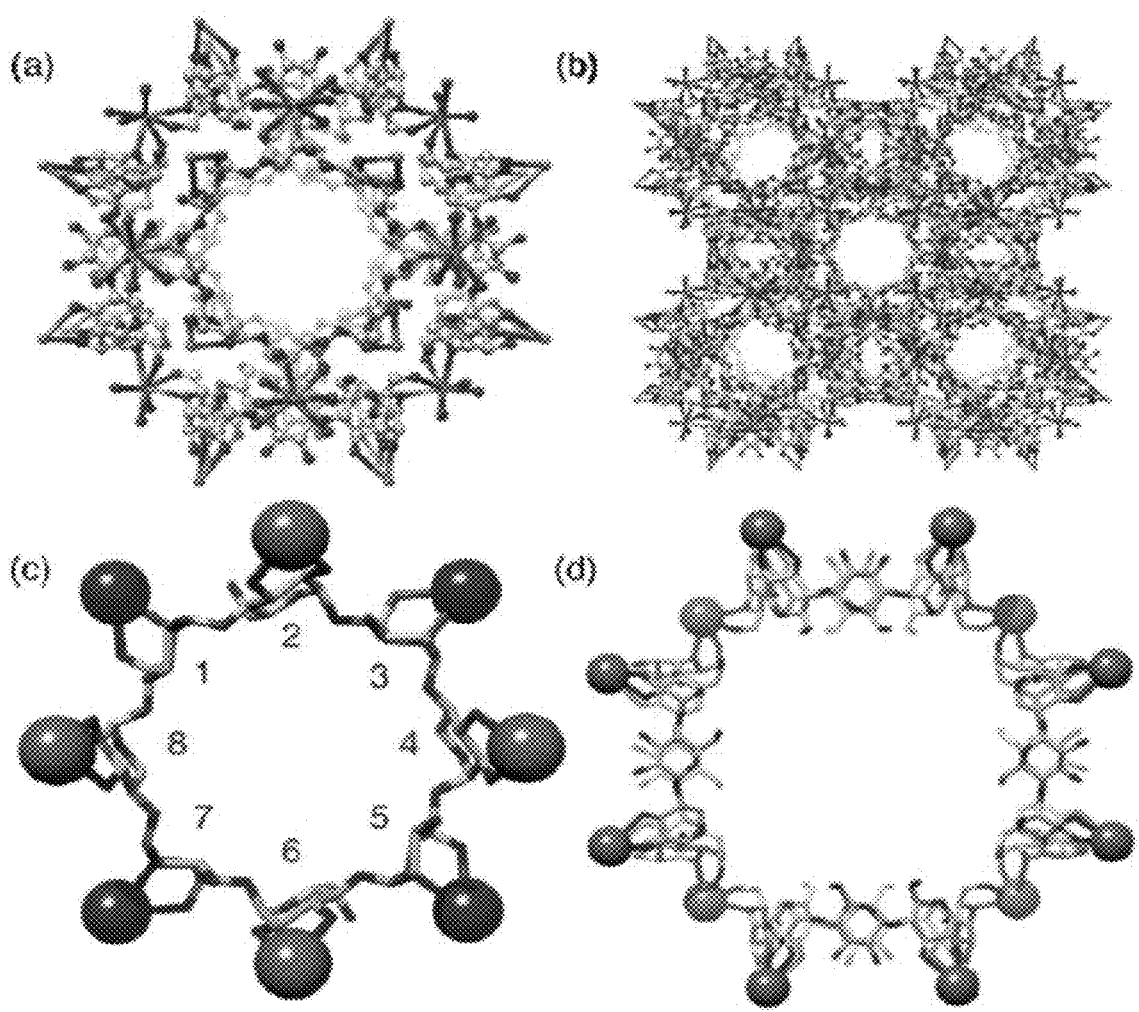
FIG. 2 depicts (a) an individual cube-shaped unit consisting of six γCD rings (γCD)$_6$, one occupying each face of the cube; (b) body-centered cubic crystal packing diagram; (c) one single γCD ring showing the K$^+$ ions bound to the primary hydroxyl group and ring oxygen atom at residues 1, 3, 5, and 7 and to the C2 and C3 hydroxyl groups at residues 2, 4, 6, and 8; and (d) cube-shaped unit with 'front' and 'back' γ-CDs removed for clarity. Crystal data of CD-MOF-1: cubic, space group I432, a=b=c=31.006(8)Å, V=29807(14)Å$^3$, Z=12.
Figure 3:
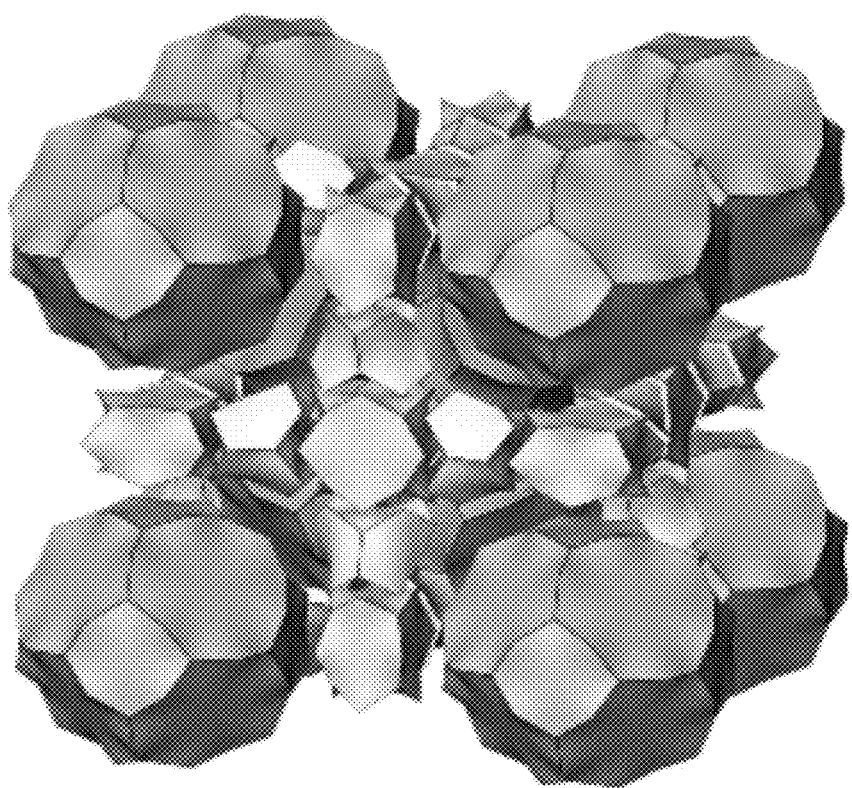
FIG. 3 is a graphical representation illustrating the different voids in the crystal structure of CD-MOF-1.

The structure in FIG. 2, CD-MOF-1, is isostructural with the structure of FIG. 1, obtained when the source of the K+ ions is K₂abdc. CD-MOF-1 is a body-centered cubic structure with each cube consisting of six γCD rings, or (γCD)₆, occupying the faces of the cube with the primary hydroxyl groups of the γCD facing into the interior of the cube. The (γCD)₆ is held together by K+ ions bonded to alternating α-d-glucopyranosyl residues, i.e., residues 1, 3, 5, and 7. Each cubic unit is attached to another one at each secondary γCD face through four K+ ions. The K+ ions are coordinated to the C2 and C3 hydroxyl groups at the 2, 4, 6, and 8 α-d-glucopyranosyl residues. The structure is a highly porous one with a regular array of large voids (FIG. 3) created by the six γCD cubic units.

Figure 12:
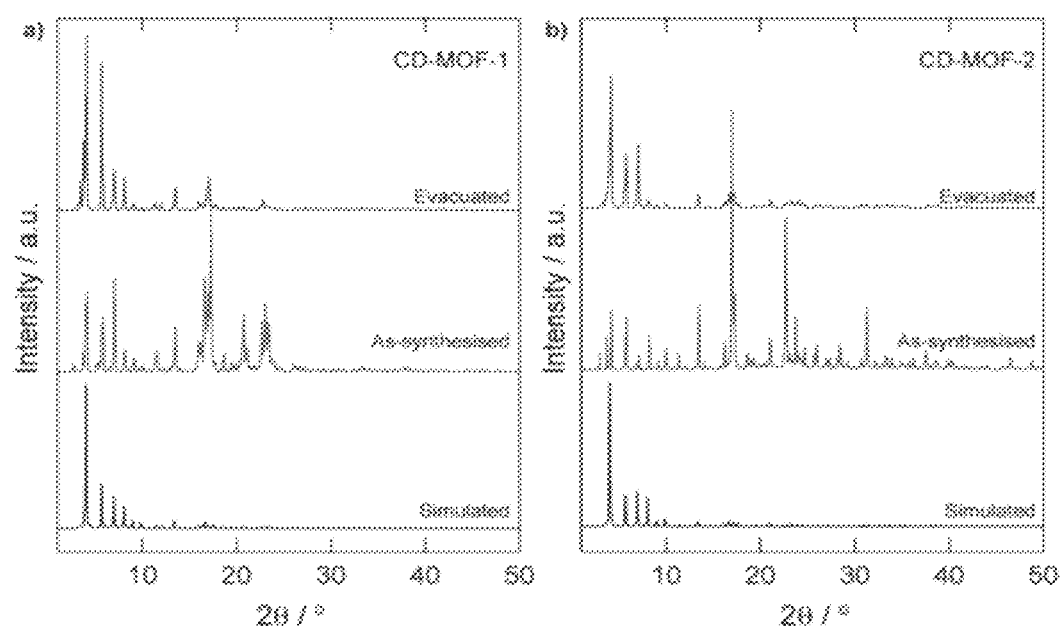
FIG. 12 shows the robustness of CD-MOF-1 and CD-MOF-2 from PXRD patterns (simulated and experimental) upon evacuation of solvent.
Figure 13:
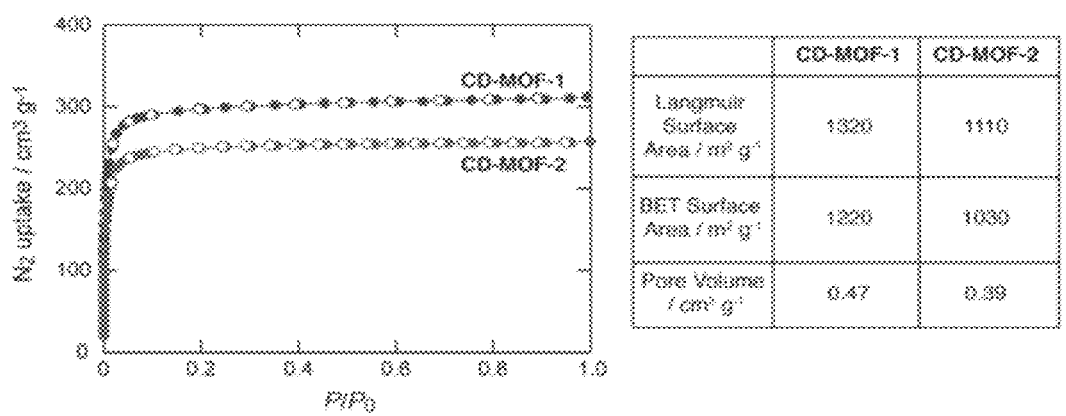
FIG. 13 $N_2$ thermal isotherm of CD-MOF-1 and CD-MOF-2 to determine BET surface area, Langmuir surface area and pore volume.

Perfect alignment of the γCDs in the structure leads to infinite channels in the x, y, and z directions with diameters equating to the inner diameter of the γCD rings, specifically 0.9 nm. The spherical pore, or cavity, contained within the six γCD cubes (γCD)₆ has a diameter of 1.7 nm. Smaller triangular pores with diameters of about 0.4 nm are present along the plane. Not surprisingly, this highly symmetrical arrangement can not be reproduced either with α- or with β-CDs, presumably since each of the eight α-d-glucopyranosyl residues in γCD is involved in binding to K+ ions. γCD is known to crystallize frequently in unusual, high symmetry space groups, e.g., P4₂₁2. Counterions and solvent molecules fill the cavities and are disordered throughout the crystal lattice. The solvent is removed from the extended structure by evacuation at room temperature (20% w/w solvent by thermogravimetric analysis) leaving robust CD-MOFs as revealed by powder x-ray diffraction patterns (FIG. 12). The BET surface area for CD-MOF-1 is 1020 m² g⁻¹ (adsorption isotherm of $CO_2$ measured for $N_2$ on CD-MOF-1; FIG. 13), while the Langmuir surface area is 1320 m² g⁻¹ and the pore volume is 0.47 cm³ g⁻¹. In comparison, the surface areas of other MOFs are: a) Basolite A100=1100 to 1500 m² g⁻¹; ZIF-95=1240 m² g⁻¹; MOF-200=10,000 m² g⁻¹; and porous polymers=~800-1000 m² g⁻¹.

Figure 4:
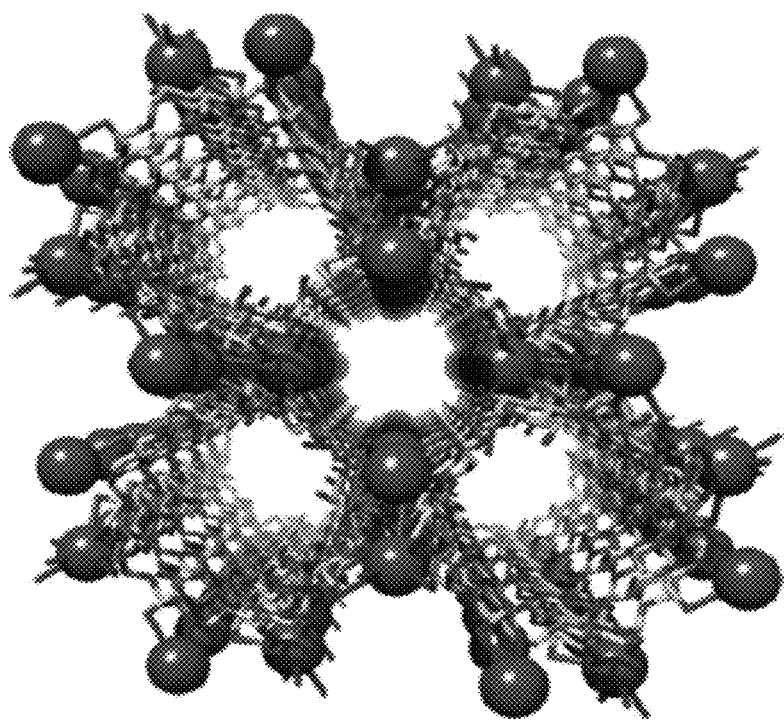
FIG. 4 shows the different nanotubes present in the crystal structure of the polymorph of CD-MOF-3.

Crystal growing experiments with NaOH/Na₂CO₃, RbOH/Rb₂CO₃, and CsOH/Cs₂CO₃ yield colorless, cubic-shaped crystals, which are examined by X-ray crystallography. The rubidium structure (CD-MOF-2) is isostructural with the potassium one, and the outcome is similar for the sodium structure. In the case of cesium, it appears that at least two different morphologies of crystals exist. One is cubic (CD-MOF-3) and is isostructural with the potassium and rubidium structures. Another batch of crystals (polymorph of CD-MOF-3), however, are needlelike and it transpires that they also have an extended MOF-like structure but, on this occasion, the cavities are oriented in a series of parallel channels; in one case defined by nanotubes of γCD rings linked by Cs+ ions, and in the other by the space left between any four γCD channels (FIG. 4).

The use of long organic struts (~2 nm) incorporating 34- and 36-membered macrocyclic polyethers as recognition modules in the construction of several crystalline primitive cubic frameworks that behave in a manner beyond open reticulated geometries (BORGs) is performed (Li, Q. et al., Science 2009 Aug. 14th Issue). The first MOF in this BORG series, MOF-1001, is capable of docking the paraquat (methyl viologen) dication within the macrocycles in a stereoelectronically controlled fashion.

Figure 5:
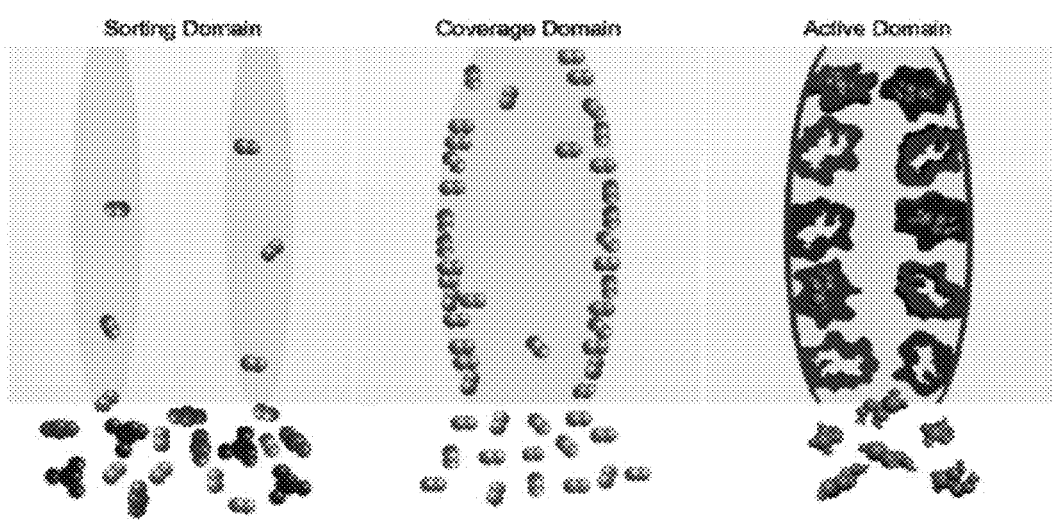
FIG. 5 is a classification of the different porous domains in metal-organic frameworks.

The vast majority of porous MOFs prepared by the methods of the invention can be regarded as having two important architectural domains: (i) the pore aperture, which is responsible for the shape- and size-selective binding of incoming molecules, and (ii) the internal surface of the pores, onto which gases or small molecules can be compacted and distributed with simple interaction sites covering the struts and joints (FIG. 5). These two domains are called the sorting domain (Kitagawa, S. et al., Angew. Chem. Int. Ed. 2004, 43, 2334-2375) and the coverage domain (Wang, Z. et al., Chem. Soc. Rev. 2009, 38, 1315-1329). In the Li et al. article, it is shown how molecular recognition components, much used in supramolecular chemistry, can be integrated in a modular fashion into the struts of MOFs, thereby creating recognition sites into which incoming guests will dock in a highly specific manner with stereoelectronic control. This third architectural domain, the active domain, combines shape, size, and electronic elements in the recognition of incoming guests and brings order to otherwise highly disordered guests in conventional MOFs.

In still another embodiment of the invention, chemical modifications of the primary hydroxyl groups on alternating glucopyranosyl residues are explored, since only one half of the primary hydroxyl groups on γCD, and likewise only one half of the secondary hydroxyl groups on C2 and C3 of the glucopyranosyl residues, are involved in coordination to the metal cations on MOF formation. This goal has been achieved (Boger, J. et al., J. Am. Chem. Soc. 1979, 7630-7631) with α-CD where selective tritylation of the CD torus has been demonstrated (Ling, C. C. et al., Carbohydrate Res. 1992, 287-291). As such, functionalizing γ-CD with post-assembly modification (fixing) of its CD-MOF superstructure is preferred. This is pursued in tandem with molecular modeling to establish the feasibility or otherwise of stabilizing the array of supramolecular nanocapsules by introducing covalent bonds between the γCD components, both within and beyond single nanocapsules. CD-MOF formation does not have to be perturbed by introducing (presumably relatively small) active functional groups onto some or all of the free hydroxyl groups.

Accordingly, in still another embodiment, the invention provides a CD-MOF comprising a CD portion and a metal salt portion; wherein the metal salt portion has the formula MN, wherein M is a Group I, Group II metal or transition metal, and N is an organic or inorganic ion; and the CD portion of CD-MOF is a compound of the Formula I:

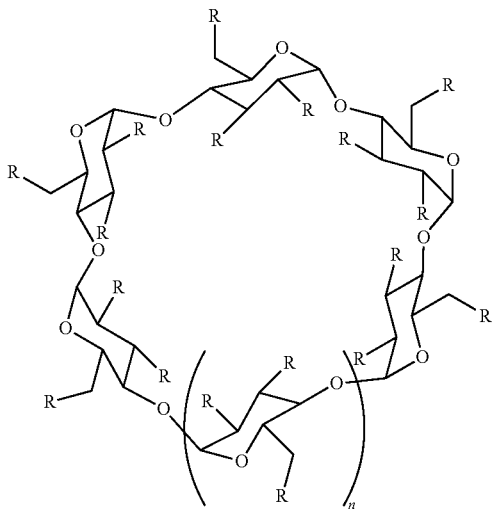

wherein n=0-10; and R is selected from the group consisting of —OH; —NR'R"; $C_1$-$C_{18}$ alkyl optionally substituted with one, two, three, four or five $R^1$ groups; $C_2$-$C_{18}$ alkenyl optionally substituted with one, two, three, four or five $R^1$ groups; $C_2$-$C_{18}$ alkynyl optionally substituted with one, two, three, four or five $R^1$ groups; $C_1$-$C_{18}$ alkoxy optionally substituted with one, two, three, four or five $R^1$ groups; —S(=O)$_2$R'; —S(=O)OR'; —S(=O)R'; —C(=O)OR'; —CN; —C(=O)R'; —SR', —N=N$^+$=N$^-$; —NO$_2$, —OSO$^2$R$^1$; —C(=O)OR', —O(=S)SR', —P(=O)(OR')$_2$; —OP(=O)(OR')$_2$; —P(=O)(OR')R"; —N=R'R"; —NR'P(OR")(OR'"); —OC(=O)NR'R"; aryl optionally substituted with one, two, three, four or five $R^2$ groups; heteroaryl optionally substituted with one, two, three, four or five groups independently selected from $R^2$ groups; and cycloalkyl optionally substituted with one, two, three, four or five groups independently selected from $R^2$ groups; wherein each $R^1$ group is independently selected from hydroxyl, halo, lower alkoxy, —NR'R", —S(=O)$_2$R', —S(=O)OR', —S(=O)R', —C(=O)OR', —CN, —C(=O)R', —N=N$^+$=N$^-$, —SR', —NO$_2$, —OSO$^2$R', —C(=O)OR', —O(=S)SR', —P(=O)(OR')$_2$, —OP(=O)(OR')$_2$; —P(=O)(OR')R", —N=R'R", —NR'P(OR")(OR'"), —OC(=O)NR'R", aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; wherein each $R^2$ group is independently selected from lower alkyl, lower alkyenyl, lower alkynyl, hydroxyl, halo, lower alkoxy, —NR'R", —S(=O)$_2$R', —S(=O)OR', —S(=O)R', —C(=O)OR', —CN, —C(=O)R', —N=N$^+$=N$^-$, —SR', —NO$_2$, —OSO$^2$R$^1$, —C(=O)OR', —O(=S)SR', —P(=O)(OR')$_2$, —OP(=O)(OR')$_2$; —P(=O)(OR')R"; —N=R'R"; —NR'P(OR")(OR'"); —OC(=O)NR'R", aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and wherein each R' and R" are independently selected from the group consisting of H, lower alkyl and aryl.

By "lower alkyl" in the present invention is meant a straight or branched chain alkyl radical having, 1-6, and preferably from 1-3, carbon atoms. Examples include but are not limited to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as, for example, a halo, cycloalkyl, aryl, alkenyl or alkoxy group and the like.

By "lower alkenyl" is meant a straight or branched hydrocarbon radical having from 2 to 6 atoms and one or two double bonds and includes, for example, ethenyl, propenyl, 1-but-3-enyl, 1-pent-3-enyl, 1-hex-5-enyl. The alkenyl group can also be optionally mono-, di-, or trisubstituted with, for example, halo, aryl, cycloalkyl or alkoxy and the like.

By "lower alkynyl" is meant a straight or branched hydrocarbon radical having from 2 to 6 atoms and one or two triple bonds and includes, for example, propynyl, 1-but-3-ynyl and the like. The alkynyl group can also be optionally mono-, di-, or trisubstituted with, for example, halo, aryl, cycloalkyl or alkoxy and the like.

By "lower alkoxy" is meant an —O-lower alkyl group wherein lower alkyl is as defined above.

By "halo" or "halogen" is meant a halogen radical of fluorine, chlorine, bromine or iodine.

By "aryl" is meant an aromatic carbocylic radical having a single ring (e.g. phenyl), multiple rings (e.g. biphenyl) or multiple fused rings in which at least one is aromatic (e.g. 1,2,3,4-tetrahydronaphthyl).

By "heteroaryl" is meant one or multiple fused aromatic ring systems of 5-, 6- or 7-membered rings containing at least one and up to four heteroatoms selected from nitrogen, oxygen or sulfur. Examples include but are not limited to furanyl, thienyl, pyridinyl, pyrimidinyl, benzimidazolyl and benzoxazolyl.

By "cycloalkyl" is meant a carbocylic radical having a single ring (e.g. cyclohexyl), multiple rings (e.g. bicyclohexyl) or multiple fused rings (e.g.). In addition, the cycloalkyl group may have one or more double bonds.

Suitable inorganic counterions are, for example, chloride, fluoride, hydroxide, sulfide, sulfinate, carbonate, chromanate, cynadie, and the like. Suitable organic counterions are, for example, benzoate, azobenzene-4,4'-dicarboxylate, acetate, oxalate, and the like.

In a further embodiment of the invention various other solvents can be used, such as, for example, dimethylformamide (DMF), dimethylsulfoxide(Me$_2$SO), diethylformamide, and any combination thereof, including with water and various low molecular weight alcohols.

Figure 6:
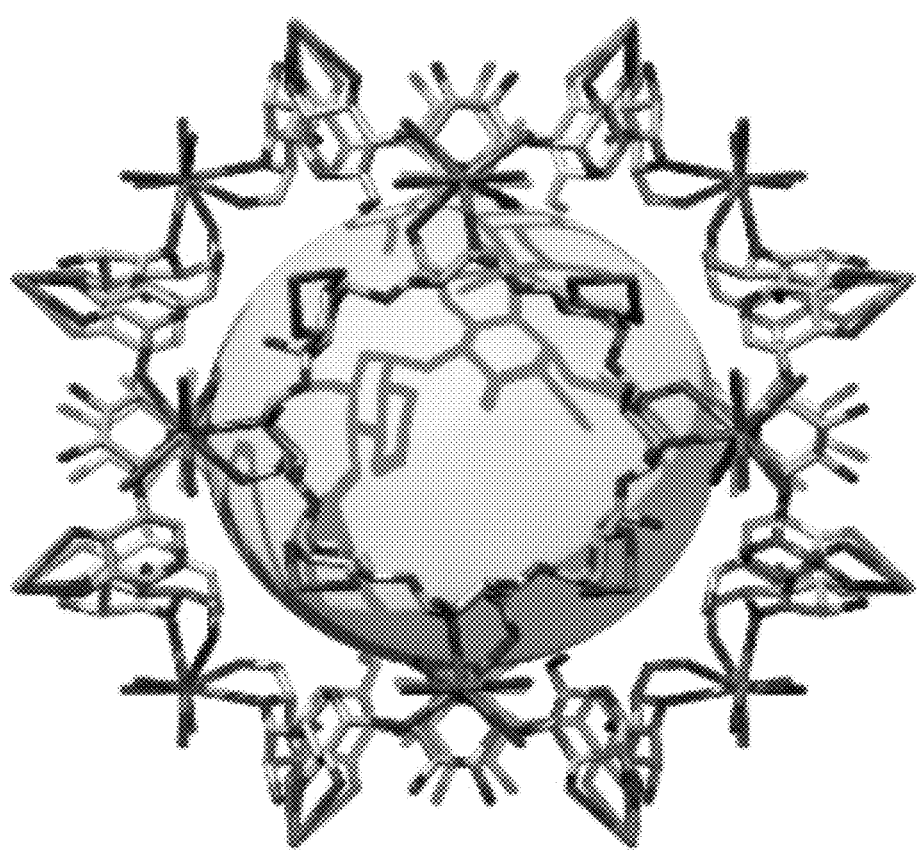
FIG. 6 is a schematic encapsulation of a gold nanoparticle in a single nanocontainer of CD-MOF-1.

In still another embodiment of the invention, the CD-MOFs incorporate molecules such as, for example, carbon dioxide, hydrogen, organophosphates, chemical warfare agents and small molecules, into the cavities and channels of the CD-MOFs, both during their self-assembly (crystallization) and after their formation, or both. In addition, particles, such as, for example, quantum dots and nanoparticles (FIG. 6) can be incorporated into the cavities and channels of CD-MOFs, both during their self-assembly (crystallization) and after their formation, or both. By incorporating these molecules or particles, the CD-MOFs provide for sequestration and/or detection of the same.

Figure 7:
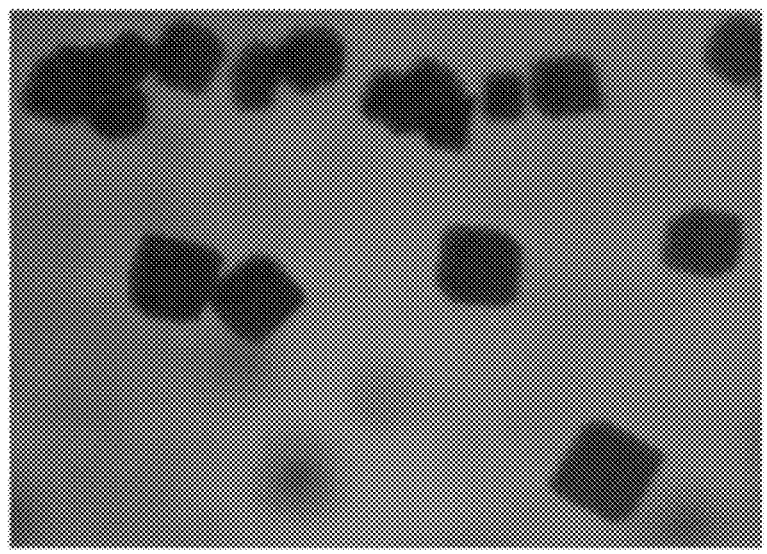
FIG. 7 depicts the deep red cubic crystals of CD-MOF-1 with encapsulated Rhodamine B guest molecules.
Figure 14:
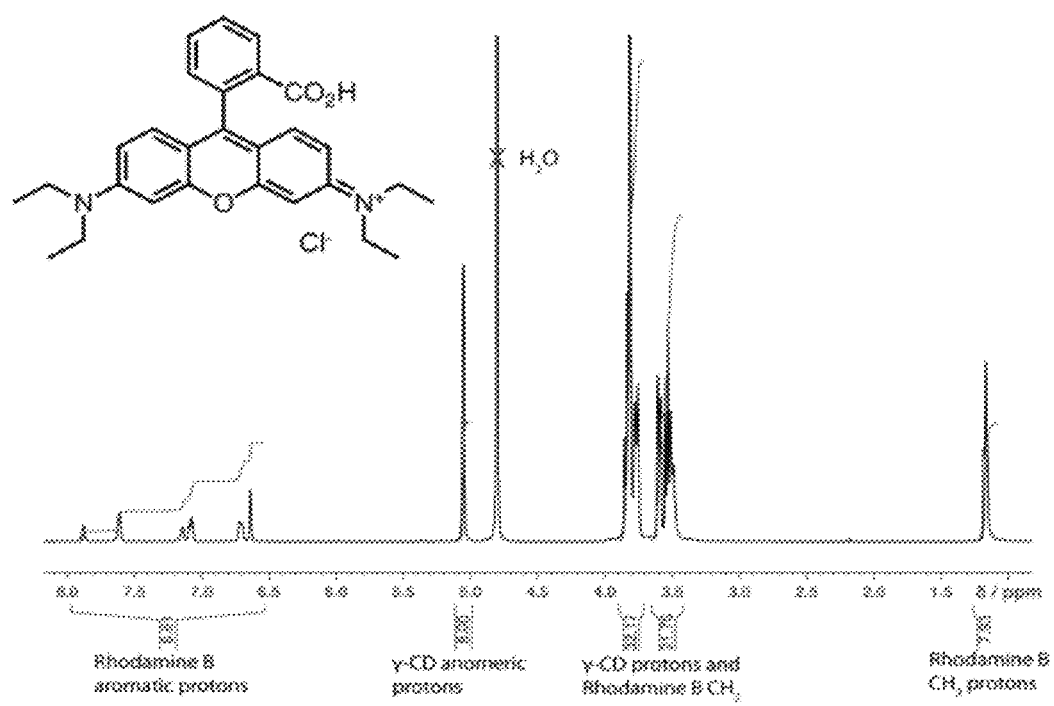
FIG. 14 $^1$H NMR Spectrum of redissolved CD-MOF-1 crystals grown in the presence of Rhodamine B dye in $D_2O$.

In a specific non-limiting example, imprinting small molecules into millimeter-sized crystals of CD-MOFs is performed in much the same way as complex core-and-shell particles are assembled into open-lattice crystals (Wesson, P. J. et al., *Adv. Mater.* 2009, 21, 1911-1915). To date, no detection of the location of substrates like pyrene and rhodamine B (FIG. 7) in the crystals by X-ray diffraction methods is seen. These small molecules remain "invisible" to X-rays, yet dissolution of these highly colored CD-MOF crystals in D$_2$O and recording $^1$H NMR spectra reveals that approximately four (4) molecules of Rhodamine B are found in each CD-MOF-1 (γCD)$_6$ cube (FIG. 14).

Figure 8:
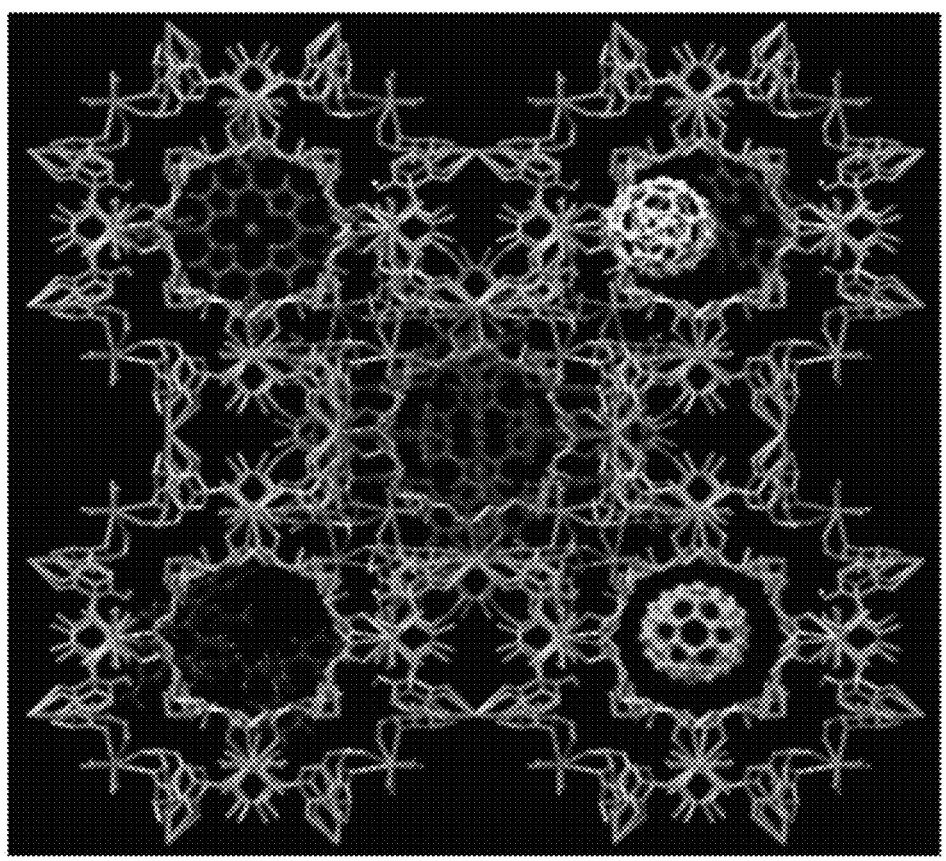
FIG. 8 is an illustration of possible guest molecules that could be incorporated into the major void spaces in CD-MOF-1.

FIG. 8 illustrates the matches that some larger molecules represent with respect to the nanochambers present in CD-MOF-1. This illustration can be used as a guide to what might be possible to incorporate (and what might not be possible) at the level of larger molecules during the crystallization of the CD-MOF in question. Some of the larger molecules, including quantum dots, nanoparticles and polyoxometalates, might act as templates for the formation of CD-MOF crystals with the molecular templates ultimately locked up inside the nanochambers of the CD-MOFs formed during the templation process.

Thus, in an embodiment of the invention, it is necessary to make use of the octahedral shape of the nanochambers to trap therein during crystallization octahedral substrates with six arms. An octahedral substrate, such as the one illustrated in FIG. 9, constitutes a suit[6]ane. Assuming that the octahedral substrate's six arms are terminated by stilbene units and that these stilbene units from different neighboring substrates meet as π-π stacked pairs (Klotz, E. J. F. et al., *J. Am. Chem.*

Soc. 2006, 128, 15374-15375; Agbaria, R. A. et al., *J. Phys. Chem. B* 1995, 24, 10056-10060) inside the two γCDs that are oriented head-to-head in the centers of the channels linking the nanochambers, following wind to join up all the stacked stilbene dimers by photochemical dimerization is possible.

Figure 9:
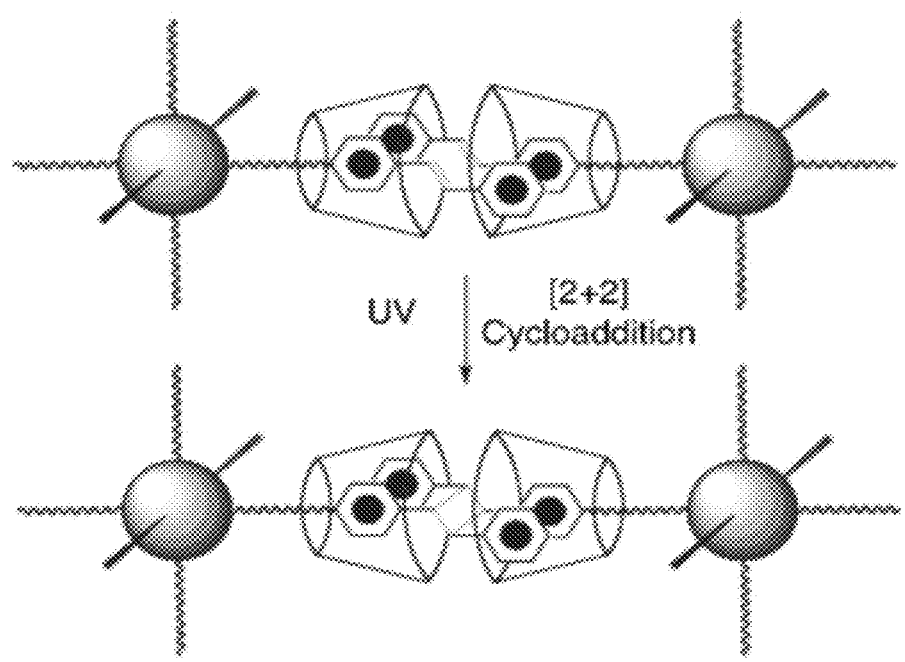
FIG. 9 is a schematic diagram showing the photolinkage of stilbene-substituted octahedral moieties, for example, hexafunctionalized fullerenes, within the CD-MOF framework.
Figure 10:
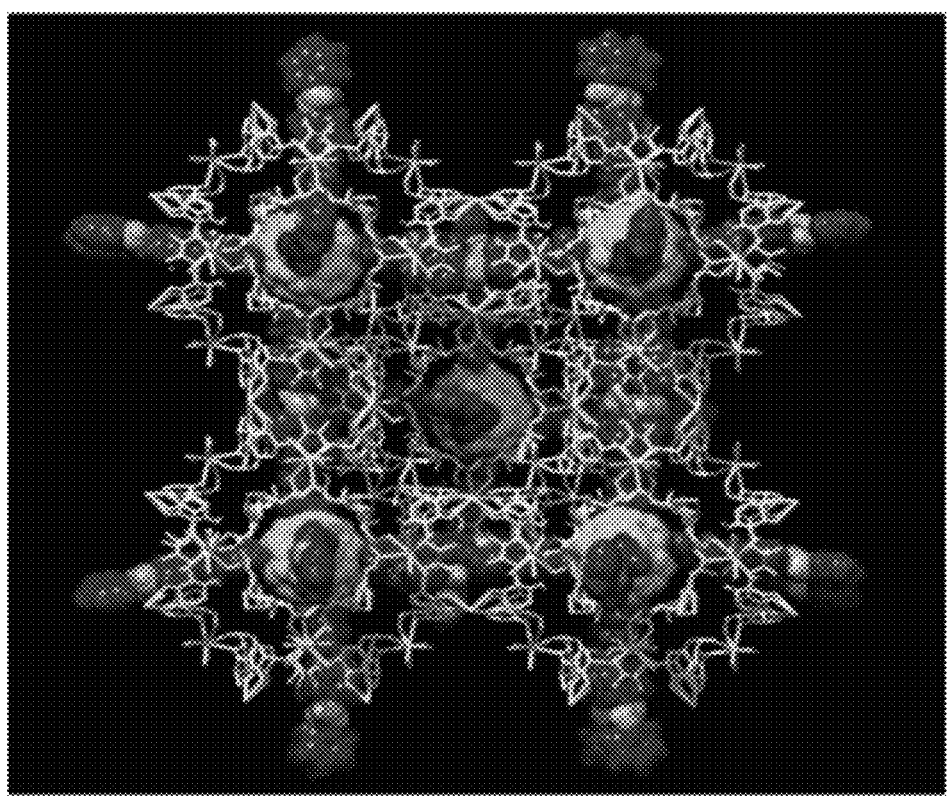
FIG. 10 depicts octahedral fullerene derivatives containing stilbene groups that can be photocrosslinked in the solid state encapsulated by the nanocontainers in CD-MOF-1.

This supramolecular control of reactivity in the solid-state has been developed elegantly by MacGillivray (MacGillivray, L. R. et al., *Acc. Chem. Res.* 2008, 41, 280-290; MacGillivray, L. R., *J. Org. Chem.* 2008, 73, 3311-3317) and Garcia-Garibay (Garcia-Garibay, M. A., *Acc. Chem. Res.* 2003, 36, 491-198) in recent times and has been applied to other supramolecular systems (Amirsakis, D. G. et al., *Angew. Chem. Int. Ed.* 2001, 40, 4256-4261; Amirsakis, D. G. et al., *Angew. Chem. Int. Ed.* 2003, 42, 1126-1132) with close to 100% efficiency for the [2+2]cycloadditions. Moreover, there are also examples of photocrosslinking of stilbenes included inside γCD in both the solution (Herrmann, W. et al., *Chem. Commun.* 1997, 1709-1710) and solid (Rao, K. et al., *J. Org. Chem.* 1999, 64, 8098-8104) states. FIG. 10 illustrates the formation of a covalent organic framework (COF) based on fullerenes inside CD-MOF-1. In still another embodiment of the invention, the making of a MOF within a MOF, where the archetypal [$Zn_4O(CO_2)_6$] cluster is the secondary building unit of the new templated MOF, is performed (FIG. 9). Washing away the alkali metal ions of the CD-MOF generates novel frameworks rotaxanated by aligned γCD dimers, whilst enzymatic cleavage of the γ-CDs generates the COF/MOF templated within the scaffold.

Sequestration and Detection of $CO_2$

The CD-MOFs as disclosed herein have a high preference for carbon dioxide over other waste gasses such as methane. By pre-incorporation of a pH-indicator, the content of carbon dioxide can be colormetrically monitored. As depicted in Formula I above, a variety of functionalized CD-MOFs, e.g. $N_1$—CDMOF, can be used to sequester and/or detect molecules such as, for example, $CO_2$. $N_1$—CDMOF is crystallographically isomorphic with CD-MOF-1.

Figure 15:
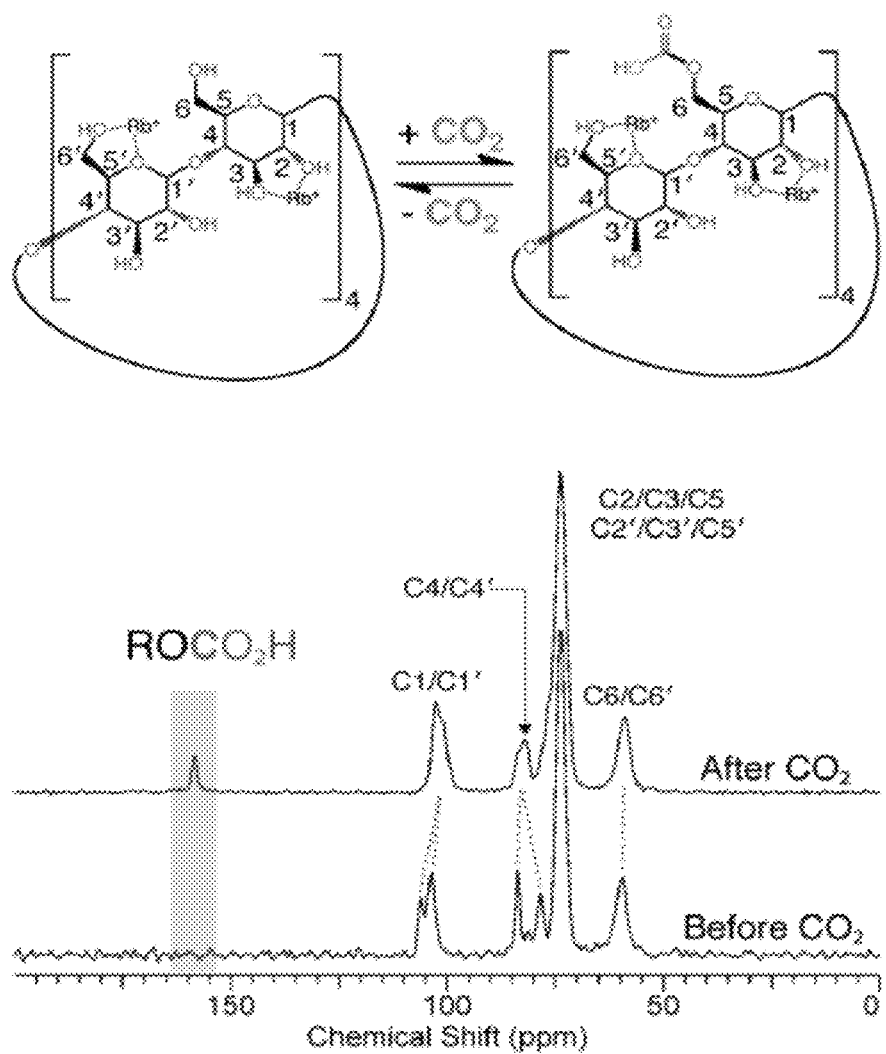
FIG. 15 CP/MAS NMR Spectrum of CD-MOF-2.

Adsorption isotherms of $CO_2$ and methane are measured for $N_2$ and $CH_4$ on both CD-MOF-1 and $N_1$—CDMOF. From the adsorption data it is clear that there is a substantial preference for carbon dioxide over methane. CP/MAS NMR Spectroscopy of CD-MOF-2 shows only signals for carbon atoms that are polarized by protons on the framework; gaseous $CO_2$ is not visible using this process (FIG. 15). 2D CP/MAS shows correlation between $^{13}$C-enriched, proposed R—$CO_3$H peak and protons on the γCD framework, indicating that the new peak is covalently attached. DP/MAS$^{13}$C NMR Spectroscopy shows all carbon atoms in the framework, including the peaks for: free gaseous $CO_2$, proposed R—$CO_3$H, and another new peak. Also, using a pH-indicator such as Methyl Red, the pH change is visually detected as $CO_2$ forms carbonic acid at primary OH on the γCD.

The gas uptake of CD-MOFs is dependent on crystallinity. Grinding a sample of CD-MOF-1 for ten (10) minutes and pulverizing it into an amorphous powder subsequently reveals no gas uptake in adsorption measurements, and no $CO_2$ uptake in CP/MAS NMR or colormetric method.

EXAMPLES

All reagents are supplied by Sigma Aldrich and Fisher, while kosher, food-grade γCD is obtained as a gift from Wacker. All chemicals and solvents are used without further purification. $^1$H Nuclear magnetic resonance (1H NMR) spectra were recorded at ambient temperature (unless noted otherwise) on a Bruker Avance 500 spectrometer, with a working frequency of 500 MHz for 1H nuclei. Chemical shifts are reported in ppm relative to the signals corresponding to non-deuterated residual solvents. Low-pressure gas adsorption experiments (up to 850 torr) are carried out on a Quantachrome AUTOSORB-1 automatic volumetric instrument. Ultrahigh-purity-grade $N_2$ and He gases are used in all adsorption measurements. $N_2$ (77 K) isotherms are measured using a liquid nitrogen bath (77 K). The pore volume of each material is estimated from the DR model with the assumption that the adsorbate is in the liquid state and that the adsorption involves a pore-filling process. Powder Xray diffraction data are collected using a Bruker D8 Discover Φ-2Φ diffractometer in reflectance Bragg-Brentano geometry at 40 kV, 40 mA (1,600 W) for Cu—Kα radiation (λ=1.5406 Å). Single crystal X-ray diffraction data is collected using a Rigaku MM007/Saturn92 diffractometer (confocal optics Cu—Kα radiation) or a Rigaku MM007/Mercury/Saturn70 diffractometer (confocal optics Mo—Kα radiation). Thermogravimetric analyses (TGA) is performed using a TA Q500 thermal analysis system at a heating rate of 5° C. $min_{-1}$ in air. Elemental analyses were performed on a Thermo Flash EA1112 combustion CHNS analyser.

Synthesis

The preparation of CD-MOFs followed the general procedure of dissolving 1.0 equiv of γCD and 8.0 equiv of the alkali metal salt in water, filtering the solution, and subsequently allowing slow vapor diffusion of MeOH into the aqueous solution to occur during several (2-7) days. The crystals that are filtered, washed with MeOH and allowed to dry in air.

CD-MOF-1—γCD (1.30 g, 1 mmol) and KOH (0.45 g, 8 mmol) are dissolved in $H_2O$ (20 mL). The aqueous solution is filtered and MeOH (ca. 50 mL) is allowed to vapor diffuse into the solution during the period of a week. Colorless cubic crystals (1.20 g, 66%), suitable for X-ray crystallographic analysis, are isolated, filtered and washed with MeOH (2×30 mL), before being left to dry in air. Elemental analysis (%) calculated for [$(C_{48}H_{80}O_{40})(KOH)_2$ $(H_2O)_8$—$(CH_3OH)_8$]n: C. 37.2, H. 7.33. found: C. 37.2, H. 7.24%. This elemental analysis data corresponds to 22% solvent composition by weight, a percentage which is commensurate with thermogravimetric analytical data that shows a weight loss of about 22% at 1008° C. A sample is dried. Elemental analysis (%) calculated for [$(C_{48}H_{80}O_{40})(KOH)_2(H_2O)_2$]$_n$: C. 39.9, H. 5.80. found: C. 39.9, H. 6.00.

CD-MOF-2—In a specific example, gγCD (1.30 g, 1 mmol) and RbOH (0.82 g, 8 mmol) are dissolved in water (20 mL). The aqueous solution is filtered and MeOH (ca. 50 mL) is allowed to vapor diffuse into the solution during the period of a week. Colorless cubic crystals (1.25 g, 71%), suitable for X-ray crystallographic analysis, are isolated, filtered and washed with MeOH (2×30 mL) before being left to dry in air. Elemental analysis (%) calculated for [$(C_{48}H_8O_{40})(RbOH)_2$ $(H_2O)_{11}$—$(CH_3OH)_2$]$_n$: C. 34.0, H. 6.40. found: C. 34.1, H. 6.32%. This elemental analysis data corresponds to 15% solvent composition by weight, a percentage which is commensurate with thermogravimetric analytical data that shows a weight loss of about 15% at 100° C. A sample is dried. Elemental analysis (%) calculated for [$(C_{48}H_{80}O_{40})(RbOH)_2$ $(CH_2Cl_2)0.5$]$_n$: C. 37.7, H. 5.42. found: C. 37.8, H. 5.24.

The synthesis of CD-MOF-3 (CsOH) is complicated by the tendency for it to crystallize alongside a related polymorph during its preparation. Solid-state structure of CD-MOF-3 is obtained by careful selection of appropriate single crystals.

A complete list of alkali metal salts used to form cubic single crystals of space group I432 and with a unit cell edge of approximately 31 Å is shown in Table 1. It is clear from the data listed in Table 1 that CD-MOF formation is almost ubiquitous amongst the myriad alkali metal salts available commercially.

TABLE 1

| Metal Salt | Ratio of Metal Salt to γCD | Unit Cell Edge/Å |
|---|---|---|
| KOH (CD-MOF-1) | 1:8 | 31.0006(8) |
| NaOH (CD-MOF-2) | 1:8 | 31.079(1) |
| CsOH (CD-MOF-3) | 1:8 | 30.868(10) |
| $Na_2CO_3$ | 1:8 | 30.751(9) |
| $K_2CO_3$ | 1:8 | 31.186(6) |
| KF | 1:8 | 30.987(8) |
| $K_2$(azabenzen-4,4'-dicarboxylate) | 1:4 | 31.040(4) |
| KCl | 1:8 | 31.161(9) |
| KBr | 1:8 | 30.946(5) |
| $NaBPh_4$ | 1:8 | 30.272(10) |

When CD-MOF-1 is prepared using potassium benzoate as a source of K+ ions, single crystal X-ray diffraction analysis revealed a trigonal space group, R32, with unit cell parameters as follows: a=b=42.6517(3), c=28.4636(5) Å, α=β=90, γ=120°. After refinement, the underlying γCD framework linked by K+ ions is found to be analogous to that of the CD-MOF-1 structures that are obtained in the cubic space group I432. The presence of 50% of the benzoate anions in the framework is observed. It is believed that the ordering of the observed benzoate counterions causes the cubic symmetry of the unit cell to be commuted, while the underlying MOF structure remains unaffected.

Single Crystal X-Ray Crystallography

Single crystal X-ray diffraction data for all MOF structures are collected at 93 K using a Rigaku MM007/Saturn92 diffractometer (confocal optics Cu—Kα radiation) for CD-MOF-2 and CD-MOF-3 at 93 K using a Rigaku MM007/Mercury/Saturn70 diffractometer (confocal optics Mo—Kα radiation) and CD-MOF-1 crystallized from solutions of potassium benzoate (vide infra). The cell dimensions for the remaining samples listed in Table 1 are also obtained from full hemisphere data collections. Intensity data is collected using ω steps accumulating area detector frames spanning at least a hemisphere of reciprocal space for all structures. Data is integrated using CrystalClear. All data is corrected for Lorentz, polarization and longterm intensity fluctuations. Absorption effects are corrected on the basis of multiple equivalent reflections. Structures are solved by direct methods and refined by full-matrix least-squares against $F^2$. Hydrogen atoms are assigned riding isotropic displacement parameters and constrained to idealized geometries.

Data for CD-MOF-1 grown from solutions of potassium benzoate are collected at 100 K using a Bruker d8-APEX II CCD diffractometer (Cu—Kα radiation). Intensity data is collected using w steps accumulating area detector frames spanning at least a hemisphere of reciprocal space for all structures. Data is integrated using SHELXTL. The cell is indexed as a superstructure, but the superstructure is proved unsolvable. The substructure is subsequently indexed and a solution is derived. Two of eight glucose rings display partial disorder, which is not resolved as a consequence of solving the substructure. This disorder resulted in isolated oxygen atoms bonded to K100 and K102 which are modeled as hydroxide anions. Structures are solved by direct methods and refined by full-matrix least-squares against $F^2$. Hydrogen atoms are assigned riding isotropic displacement parameters and constrained to idealised geometries.

Thermal Stability and Activation

In order to remove interstitial solvents, as-synthesized samples of CD-MOF-1 and CD-MOF-2 are immersed in $CH_2Cl_2$ for three days. During the solvent exchange process, the $CH_2Cl_2$ is refreshed three times. The resulting $CH_2Cl_2$-exchanged sample of each CD-MOF is transferred as a suspension to a quartz cell and the solvent decanted. The wet sample is then evacuated ($10^{-3}$ Torr) at room temperature for 10 hours, and then at 45° C. for 12 hours.

Figure 16:
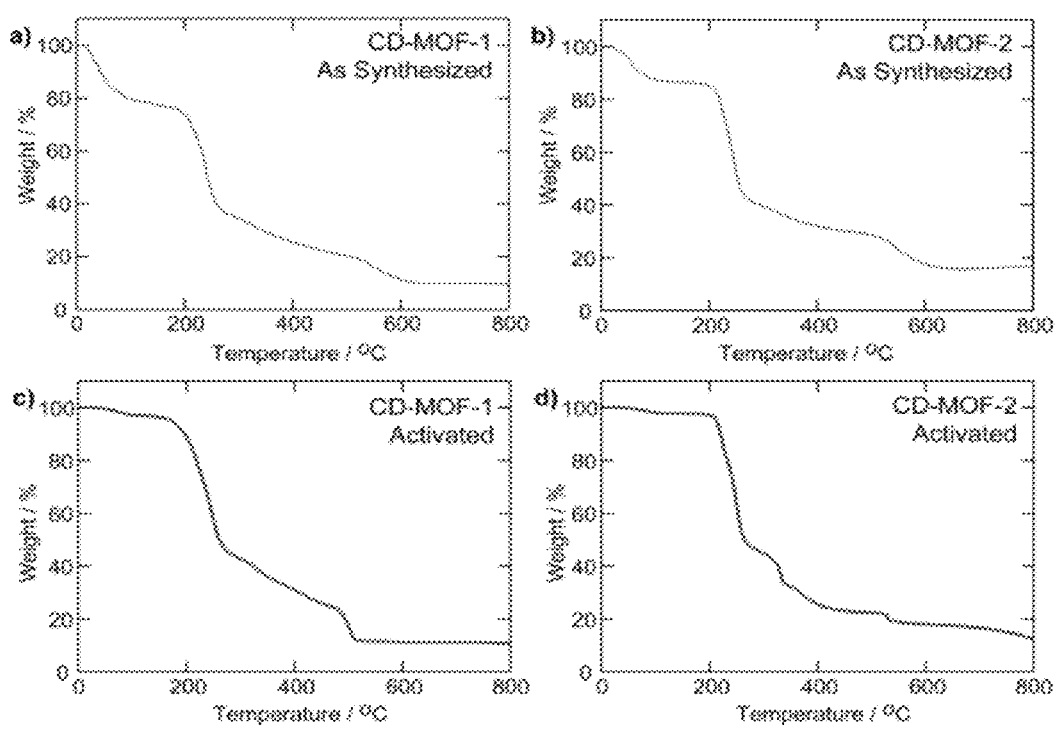
FIG. 16 Thermogravimetric analysis traces of CD-MOF-1 and CD-MOF-2; 16a-b confirm the retention of solvent in both CD-MOF-1 and CD-MOF-2, respectively; 16c-d show the stability of activated CD-MOF-1 and CD-MOF-2, respectively, to heating.

The stabilities of as-synthesized and activated samples of CD-MOF-1 and CD-MOF-2 are examined by thermogravimetric analysis (TGA) under oxidative conditions. The retention of solvents by CD-MOF-1 and CD MOF-2 evident in their respective TGA traces (FIGS. 16a and 16b) are commensurate with values obtained by elemental analysis, and they also show thermal stability of the frameworks, after solvent loss, up to temperatures of approximately 175° C. for CD-MOF-1 and 200° C. for CD-MOF-2. The stability of activated CD-MOF-1 to heating is illustrated in its TGA trace (FIG. 16c), which shows retention of mass until approximately 175° C., with a 2.4% loss in mass at approximately 100° C. corresponding to the loss of two $H_2O$ molecules per γCD ring. Retention of small amounts of water by CD-MOF-1 through the activation process may occur as a result of γCD's great affinity for water, or indeed this small amount of water present in the sample can be explained by deliquescence after the activation process. Thermal degradation occurs at temperatures over 175° C. An analogous experiment (FIG. 16d) with CD-MOF-2 yields similar results, with thermal stability of the sample at temperatures under 200° C. confirmed. A small (0.6%) drop in mass at approximately 100° C. indicates the presence of approximately 0.5 molecules of $H_2O$ per γCD ring, again presumably on account of deliquescence.

$^1$H NMR Spectroscopy—Determination of Counterions

Potassium salts of the benzoate monoanion and the azobenzene-4,4'-dicarboxylate dianion yield single crystals, whose CD-MOF framework structures are confirmed by X-ray diffraction. The crystals are then dried, dissolved in $D_2O$ and the $^1$H NMR spectra of the solutions recorded.

Figure 17:
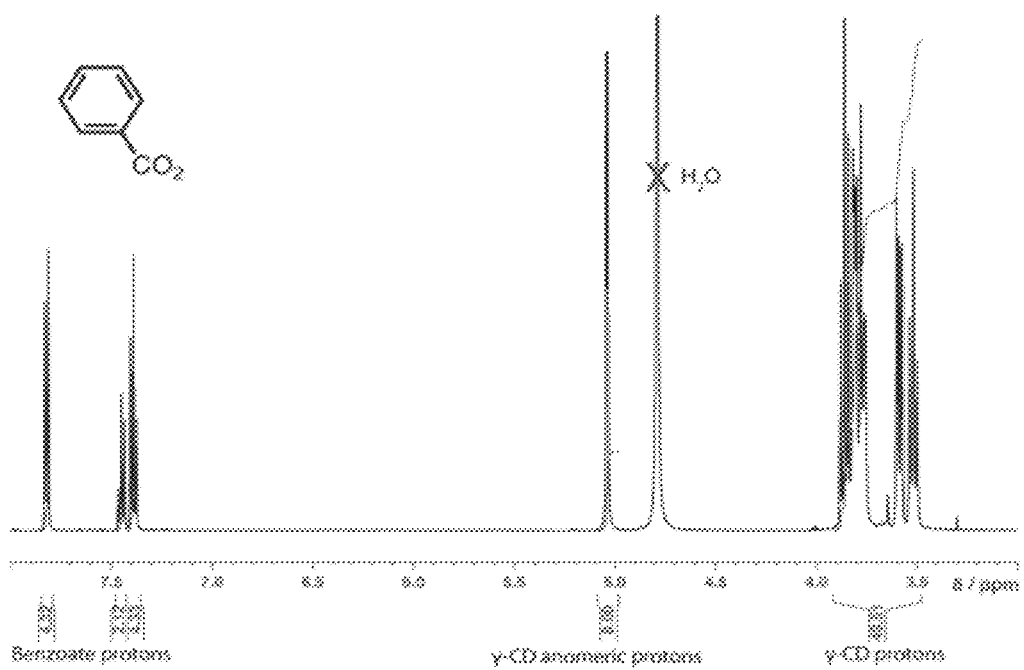
FIG. 17 $^1$NMR spectrum (500 MHz) in $D_2O$ of redissolved CD-MOF crystals prepared from potassium benzoate and γCD, referenced to the $H_2O$ peak (&=4.79).

Potassium benzoate—colorless, cubic crystals are grown by dissolving γCD (0.26 g, 0.2 mmol) and potassium benzoate (0.256 g, 1.6 mmol) in water (5 mL), filtering the colorless solution and allowing MeOH vapors to diffuse in slowly over approximately 5 days. The crystals are isolated by filtration and washed twice with MeOH (2×10 mL) to remove excess of potassium benzoate. The crystals are dried in vacuo, dissolved in $D_2O$ and subjected to analysis by $^1$H NMR spectroscopy (FIG. 17).

When the integral for the anomeric protons (δ~5) of the γCD units is set to eight, representing one γCD torus, the remaining 48 γCD protons (δ~3.5-4.0) integrate to ~49.5. The benzoate aromatic signals have a combined integral of 10.7, which corresponds to approximately two benzoate anions (5 protons are present in each molecule). This integral represents a ratio of two benzoate monoanions, and thus, two K+ cations, to one γCD unit, corresponding to the ratio of K+ cations to γCD tori observed in the crystal structure of CD-MOF-1.

Dipotassium Azobenzene-4,4'-Dicarboxylate—Orange, cubic crystals are grown by dissolving γCD (0.26 g, 0.2 mmol) and dipotassium azobenzene-4,4'-dicarboxylate (278 mg, 0.8 mmol) in water (5 mL), filtering the orange solution and allowing MeOH vapors to diffuse in slowly over approximately 5 days. The crystals are isolated by filtration and washed twice with MeOH (2×10 mL) to remove excess of dipotassium azobenzene-4,4'-dicarboxylate. The crystals are dried in vacuo, dissolved in $D_2O$ and subjected to analysis by $^1H$ NMR spectroscopy (FIG. 11).

When the integral for the anomeric protons (δ~5) of the γCD units is set to eight, representing one γCD torus, the remaining 48 γCD protons (δ~3.5-4.0) integrated to 49.5. Both the cis and trans isomers of azobenzene-4,4'-dicarboxylate are observed in the spectrum; the total integral is 8.44 for all the protons in the molecule. Since azobenzene-4,4'-dicarboxylate has eight protons in total, this integral represents a ratio of one azobenzene-4,4'-dicarboxylate dianion, i.e., two $K^+$ cations, to one γCD unit, corresponding to the ratio of $K^+$ cations to γCD tori observed in the crystal structure of CD-MOF-1. The significance of this ratio is underscored by conducting a second experiment, wherein double the quantity of dipotassium azobenzene-4,4'-dicarboxylate is employed in the initial crystallization process. The $^1H$ NMR spectrum of the dissolved crystals once again show the same ratio of anion to γCD, despite the doubling of their amount in the starting material. These experiments provide strong evidence that benzoate and azobenzene-4,4'-dicarboxylate act as the counterions in their respective CD-MOF-1 frameworks. The these ratios of counterions correspond to 12 benzoate anions or six azobenzene-4,4"-dicarboxylate anions per $(\gamma CD)_6$ cube.

Small Molecule Co-Crystallization

Rhodamine B is used to study the co-crystallization of dye molecules within the CD-MOF-2 framework. γCD (0.26 g, 0.2 mmol) and RbOH (0.164 g, 1.6 mmol) are dissolved in water (5 mL), and Rhodamine B (ca. 0.25 g) is added until the aqueous solution is saturated. After filtration, MeOH vapors are allowed to diffuse into the red solution and deep red crystals form during 5 days. The crystals are isolated by filtration and washed with MeOH (2×20 mL). Subsequently, the crystals are washed with 20 mL portions of $CH_2Cl_2$ until no red color is evident in the washings, ensuring that all excess of Rhodamine B is removed prior to analysis. The crystals are dried in vacuo, dissolved in $D_2O$ and examined (FIG. 14) by $^1H$ NMR spectroscopy.

The integral for the anomeric protons (δ~5) of the γCD units is set to eight, representing one γCD torus. The integral for the characteristic Me protons (δ=1.15) of the Rhodamine B diethylamino groups also integrate for approximately eight, and so, since each molecule of Rhodamine B has 12 Me protons, this integral suggests a ratio of two Rhodamine B molecules for every three γCD molecules. The total integration of the Rhodamine B aromatic protons (δ~6.5-8.0) is 6.6, and considering that each molecule has 10 aromatic protons, the integral once again indicates the 2:3 ratio. The signals for the $CH_2$ protons of the Rhodamine B diethylamino groups overlap with the remaining signals from the γCD ring, resulting in a total integral of ~54. Subtracting the expected value of 48 for the γCD protons leaves an integral of approximately 6 for the Rhodamine B $CH_2$ protons, of which there are eight in the molecule. Using the 2:3 ratio of Rhodamine B to γCD molecules, an integral of 5.3 is expected.

In broader terms, this 2:3 ratio indicates a loading of four Rhodamine B molecules per $(\gamma CD)_6$ cube. Although X-ray crystallography confirms the structure of CD-MOF-2 is unaffected by dye co-crystallization, the arrangement of the Rhodamine B molecules within the solid state structure of CD-MOF-2 can not be determined, because of their disorder within the vast framework.

Small Molecule Adsorption

4-Phenylazophenol, an orange azobenzene-based dye, is used to observe the uptake of small molecules from $CH_2Cl_2$ solution by CD-MOF-2 crystals. As-synthesized crystals are activated by replacing the MeOH/$H_2O$ solvent with $CH_2Cl_2$, in order to exchange all interstitial solvents. This procedure is carried out without exposing the colorless crystals to air in order to minimize cracking. The crystals are soaked in $CH_2Cl_2$ for three days, after which a saturated solution of 4-phenylazophenol in $CH_2Cl_2$ is used to replace the original $CH_2Cl_2$, and the crystals are allowed to soak for a another 24 hours. The crystals are isolated by filtration and washed with $CH_2Cl_2$ until no color is evident in the washings, indicating no excess of 4-phenylazophenol remaining. The crystals are dried in vacuo, dissolved in $D_2O$ and analyzed by $^1H$ NMR spectroscopy.

Following the protocol used for previous experiments, the integral for the anomeric protons (δ~5) of the γCD units is set to eight, representing one γCD torus. The total integral of the 4-phenylazophenol aromatic protons (δ~6.5-8.0) is 6.42 when there are nine aromatic protons in each molecule. This observation results in a ratio of approximately 4.3 molecules of 4-phenylazophenol present with respect to each $(\gamma CD)_6$ cube, similar to the value of four molecules of Rhodamine B per $(\gamma CD)_6$ cube measured from co-crystallization experiments.

Preparation of "Edible" CD-MOFs

Food grade crystals of CD-MOF-1 are prepared by dissolving commercially available foodgrade potassium benzoate (283 mg, 1.8 mmol) and food-grade γCD (2.30 g, 1.8 mmol) in distilled water. The aqueous solution is filtered through cotton wool and, following vapor diffusion of Everclear grain alcohol into the solution over a few days, crystals of CD-MOF-1 are obtained. These crystals represent a MOF that is comprised of entirely food grade reagents.

$N_2$ Adsorption Isotherms

Isotherms are measured for both $CO_2$ and $CH_4$ on CD-MOF-2 at incremental temperatures (FIG. 17). The total uptake of $CO_2$ in the low pressure region (<0.01 Torr) is clearly unaffected over the temperature range from 273 K to 298 K, remaining at approximately 23 $cm^3/g$, regardless of sample temperature. Additionally, the steep slope of the isotherm in this region suggests a strong binding event, one that would equate with the formation of a carbon-carbon bond. Notably, the abrupt transition in higher pressure regimes (>1 Torr) becomes much more dependent upon temperature, as indicated by a 30% greater uptake of $CO_2$ at 273 K compared to 298 K. These observations are consistent with covalent bond formation occurring preferentially at low pressures. Chemisorption gives way to physisorption at elevated pressures with the change in mechanism of uptake occurring at 23 $cm^3/g$.

CP/MAS NMR

Spectroscopic evidence showing the solid-state reactivity of γCD with $CO_2$ is obtained by cross polarizing magic angle spinning (CP/MAS) NMR spectroscopy. Crystalline samples are activated by exchanging the aqueous methanolic solution with dichloromethane (DCM) before being evacuation and drying at low pressure (<$2.0 \times 10^{-3}$ Torr) for two days to remove remaining water. The activated CD MOF-2 is exposed to an atmosphere of dry $CO_2$ for 10 minutes and transferred into an airtight zirconium solid-state NMR rotor. The $^{13}C$ NMR spectrum of crystalline samples of activated CD-MOF-2 show (FIG. 17) separate peaks for C1 and C1', as well as for C4 and C4', as a result of the commuted symmetry induced by the alternating $Rb^+$ cations on the primary and secondary faces of the γCD tori. Upon exposure to $CO_2$ a new peak emerges, centered on 158 ppm, in the form of a resonance which is known to be consistent with carbonate formation. Furthermore, peaks associated with the C1 and C1' carbons, as well as the C4 and C4' carbons, undergo appreciable changes in their chemical shift, reflecting the fact that a chemical reaction has occurred on the γCD tori.

Figure 18:
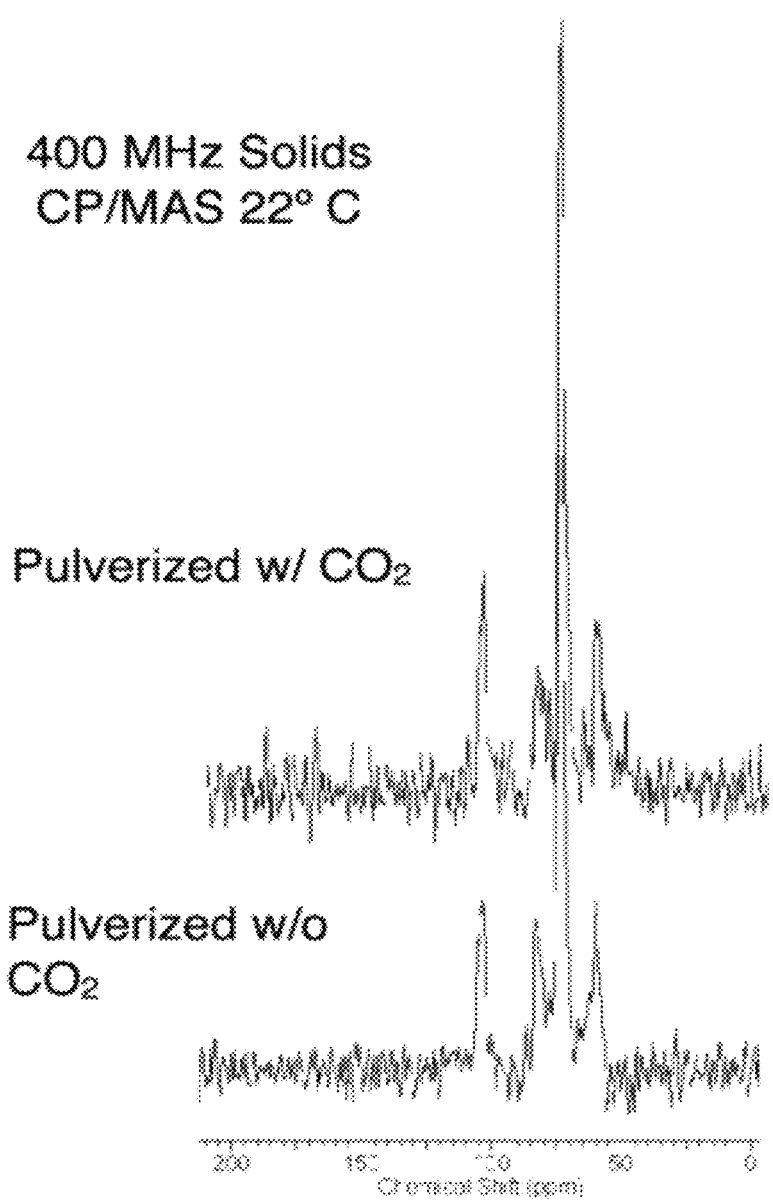
FIG. 18 CP/MAS NMR spectrum of ground samples of CD-MOF-2.
Figure 19:
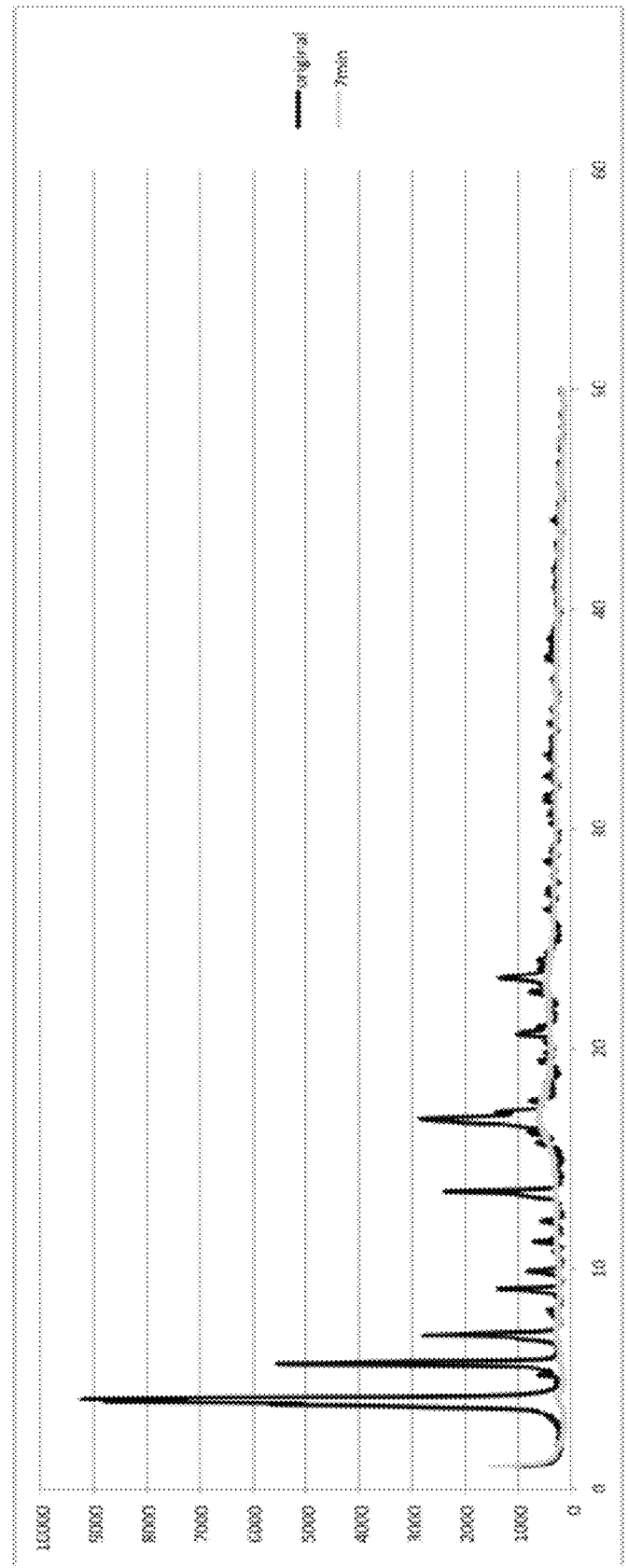
FIG. 19 Powder x-ray diffraction of a ground sample of CD-MOF-2.

It is speculated that this favorable reactivity arises because the γ-CD of CD-MOF-2 bear primary hydroxyl groups which define the circumference of a large (1.7 nm diameter) pore. The accessibility of these hydroxyl groups in the crystalline state far exceeds that of the amorphous state, as determined by Langmuir and BET analysis. For example, no evidence of carbonate formation is observed by CP/MAS NMR spectroscopy on pure γCD after exposure to $CO_2$. Indeed, literature reports suggest that the reaction to form carbonic acid from $CO_2$ with cyclodextrins is not a favorable one. In order to establish that the reactivity of CD-MOF-2 with $CO_2$ is dependent on crystallinity, samples are ground in a mortar and pestle for 10 minutes, before being exposed to $CO_2$ and analyzed by CP/MAS NMR spectroscopy. This experiment reveals that neither new resonances nor changes to the original signals are observed, indicating (FIG. 18) that no carbonate formation occurs. Analysis of the ground sample by powder X-ray diffraction shows (FIG. 19) crystallinity is lost after seven minutes of continuous dry grinding, which renders the sample into an amorphous state, yet it retains the same ratios of rubidium salts and γCD that are present in the original sample.

Methyl Red pH Indicator

Methyl red, a zwitterionic azobenzene based pH indicator, is diffused into the pores of CD-MOF-2 by suspension in a DCM solution of the dye. The red solution is decanted and the crystals are washed and dried in vacuo, affording brilliant yellow crystals. The yellow color arises from the incorporated methyl red undergoing partial anion metathesis and, consequently, depronation, with the hydroxide counterions in the pore structure. $^1$H NMR spectroscopy shows that the incorporation of methyl red into CD-MOF-2 is no more than 10% by weight and BET analysis of the activated samples indicates that incorporation of the pH indicator reduces the surface area by 50%. The dried crystals are transferred to a scintillation vial, which is then exposed to both dry (from a tank) and humid (sublimed dry ice) $CO_2$ vapor. The initial color change from yellow to orange/red occurs quickly, regardless of the $CO_2$ source, and, after five minutes, no further color change can be discerned by the naked eye. When the source of $CO_2$ is removed, the crystals revert to a yellow color, indicating that the transient carbonic acid function is reverted to the alcohol, liberating $CO_2$. This process is repeated many times and no apparent fatigue is observed on the material.

As a control, the same experiment is performed on crystals of CD-MOF-5, which are loaded with the ammonium salt of methyl red. The structure of CD-MOF-5-$Zn_4O$ clusters linked by terephthalate dianions—does not contain any free hydroxyl or amino groups capable of forming an acid moeity to elicit a pH-based color change, and therefore would not be expected to demonstrate chemisorption. The presence of $CO_2$ has no effect on crystal color, indicating that no chemisorption is occurring. To rule out the possibility that the more nucleophilic hydroxide counterion is the reactive agent forming carbonate anions by reaction with $CO_2$, crystals of so-called "edible-CD-MOF," which are isostructural with CD-MOF-2 but are synthesized from potassium benzoate, are used. After activation and removal of solvent, the crystals of edible CD-MOF changed color reversibly within the same time frame. CP/MAS spectroscopy on edible CD-MOF is performed as well, and the carbonate resonance appearing 158 ppm appears—precisely the same chemical shift found in CD-MOF-2 when exposed to $CO_2$.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A γ-cyclodextrin-based metal-organic framework comprising a plurality of metal cations and a plurality of γ-cyclodextrin molecules or a plurality of γ-cyclodextrin derivative molecules coordinated to the plurality of metal cations, the γ-cyclodextrin-based metal-organic framework being porous, wherein the γ-cyclodextrin or γ-cyclodextrin derivative is a compound of the Formula I:

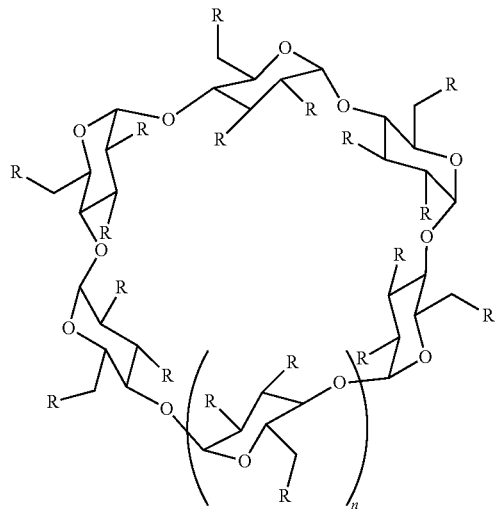

wherein
n=2; and
R is selected from the group consisting of —OH; —NR'R"; —S(=O)$_2$R'; —S(=O)OR'; —S(=O)R'; —C(=O)OR'; —CN; —C(=O)R'; —SR', —N=N$^+$=N$^-$; —NO$_2$, —OSO$^2$R'; —C(=O)OR', —O(=S)SR', —P(=O)(OR')$_2$; —OP(=O)(OR')$_2$; —P(=O)(OR')R"; —N=R'R"; —NR'P(OR")(OR'''); —OC(=O)NR'R"; $C_1$-$C_{18}$ alkyl optionally substituted with one, two, three, four or five R$^1$ groups; $C_2$-$C_{18}$ alkenyl optionally substituted with one, two, three, four or five R$^1$ groups; $C_2$-$C_{18}$ alkynyl optionally substituted with one, two, three, four or five R$^1$ groups; $C_1$-$C_{18}$ alkoxy optionally substituted with one, two, three, four or five R$^1$ groups; aryl optionally substituted with one, two, three, four or five R$^2$ groups; heteroaryl optionally substituted with one, two, three, four or five groups independently selected from R$^2$ groups; and cycloalkyl optionally substituted with one, two, three, four or five groups independently selected from R$^2$ groups; wherein
each R$^1$ group is independently selected from hydroxyl, halo, lower alkoxy, —NR'R", —S(=O)$_2$R', —S(=O)OR', —S(=O)R', —C(=O)OR', —CN, —C(=O)R', —N=N$^+$=N$^-$, —SR', —NO$_2$, —OSO$^2$R', —C(=O)OR', —O(=S)SR', —P(=O)(OR')$_2$, —OP(=O)(OR')$_2$; —P(=O)(OR')R", —N=R'R", —NR'P(OR")(OR'''), —OC(=O)NR'R", aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups;

each $R^2$ group is independently selected from lower alkyl, lower alkyenyl, lower alkynyl, hydroxyl, halo, lower alkoxy, —NR'R", —S(=O)$_2$R', —S(=O)OR', —S(=O)R', —C(=O)OR', —CN, —C(=O)R', —N=N$^+$=N$^-$, —SR', —NO$_2$, —OSO$^2$R', —C(=O)OR', —O(=S)SR', —P(=O)(OR')$_2$, —OP(=O)(OR')$_2$; —P(=O)(OR')R"; —N=R'R"; —NR'P(OR")(OR'''); —OC(=O)NR'R", aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and each R' and R" are independently selected from the group consisting of H, lower alkyl and aryl, wherein the γ-cyclodextrin-based metal organic framework has a crystal structure with a I432 space group.

2. A γ-cyclodextrin-based metal-organic framework of claim 1 wherein the metal cations are selected from the group consisting of Li$^+$, K$^+$, Rb$^+$, Cs$^+$, Na$^+$, Mg$^{2+}$, Cd$^{2+}$, Sn$^{2+}$, Ag$^+$, Yb$^+$, Ba$^{2+}$, Sr$^{2+}$, Ca$^{2+}$, Pb$^{2+}$, and La$^{3+}$.

3. A γ-cyclodextrin-based metal-organic framework of claim 2 wherein the metal cations are selected from the group consisting of K$^+$, Rb$^+$, Cs$^+$ and Na$^+$.

4. A γ-cyclodextrin-based metal-organic framework of claim 1 further comprising a counterion that is an organic or inorganic molecule.

5. A γ-cyclodextrin-based metal-organic framework of claim 4 wherein the counterion is inorganic and selected from the group consisting of —OH and $CO_3^{-2}$.

6. A γ-cyclodextrin-based metal-organic framework of claim 4 wherein the counterion is organic and selected from the group consisting of benzoate anion and azobenzene-4,4'-dicarboxylate dianion.

7. A γ-cyclodextrin-based metal-organic framework of claim 1 forming a single cubic crystal.

8. A γ-cyclodextrin-based metal-organic framework of claim 7 wherein the cubic crystal has a unit cell edge of approximately 31 Å.

9. A γ-cyclodextrin-based metal-organic framework of claim 1 wherein the γ-cyclodextrin rings form a central pore.

10. A γ-cyclodextrin-based metal-organic framework of claim 9 wherein the central pore has a diameter of approximately 1.7 nm.

11. A γ-cyclodextrin-based metal-organic framework of claim 10 further comprising a plurality of smaller triangular pores with diameters of approximately 0.4 nm.

12. A γ-cyclodextrin-based metal-organic framework of claim 11 wherein counterions fill the pores and channels of the metal organic framework and are disordered throughout the crystal lattice.

13. A γ-cyclodextrin-based metal-organic framework of claim 12 wherein solvent molecules fill the pores and channels of the metal organic framework and are disordered throughout the crystal lattice.

14. A γ-cyclodextrin-based metal-organic framework of claim 11 wherein particles fill the pores and channels of the metal organic framework.

15. A γ-cyclodextrin-based metal-organic framework of claim 14 wherein the particles are selected from the group consisting of quantum dots and nanoparticles.

16. A γ-cyclodextrin-based metal-organic framework of claim 1 selected from the group consisting of: a) K$^+$ as the metal cation, OH$^{-1}$ as the couneranion and γ-cyclodextrin; b) Rb$^+$ as the metal cation, OH$^{-1}$ as the couneranion and γ-cyclodextrin; c) Cs$^+$ as the metal cation, OH$^{-1}$ as the couneranion and γ-cyclodextrin.

17. A γ-cyclodextrin-based metal-organic framework of claim 1 for sequestering or detecting a molecule or particle either during self-assembly of the cyclodextrin-based metal organic framework or after formation of the cyclodextrin-based metal organic framework, or both.

18. A γ-cyclodextrin-based metal-organic framework of claim 4 wherein the counterion is a colorimetric pH indicator used as a means of detecting formation of organic or inorganic acid functions within the framework or on the framework.

* * * * *